(12) United States Patent
Conway

(10) Patent No.: US 7,524,308 B2
(45) Date of Patent: Apr. 28, 2009

(54) SAFETY SHIELDING NEEDLE ASSEMBLY WITH PASSIVE SHIELDING

(75) Inventor: Hugh T. Conway, Verona, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 203 days.

(21) Appl. No.: 10/820,275

(22) Filed: Apr. 8, 2004

(65) Prior Publication Data

US 2004/0210197 A1 Oct. 21, 2004

Related U.S. Application Data

(60) Provisional application No. 60/463,384, filed on Apr. 16, 2003.

(51) Int. Cl.
   A61M 5/32 (2006.01)
   A61M 5/00 (2006.01)
(52) U.S. Cl. .................................. 604/192; 604/110
(58) Field of Classification Search .............. 604/187, 604/110, 263, 264, 192–198; 600/576, 578
   See application file for complete search history.

(56) References Cited

U.S. PATENT DOCUMENTS

| 4,887,998 | A | * | 12/1989 | Martin et al. | ............... | 604/110 |
|---|---|---|---|---|---|---|
| 5,713,239 | A | | 2/1998 | Kirschner | | |
| 5,893,845 | A | | 4/1999 | Newby et al. | | |
| 6,984,223 | B2 | * | 1/2006 | Newby et al. | ............... | 604/263 |
| 7,118,552 | B2 | * | 10/2006 | Shaw et al. | ................. | 604/110 |
| 2004/0111068 | A1 | * | 6/2004 | Swenson | ..................... | 604/263 |

FOREIGN PATENT DOCUMENTS

| EP | 1 208 862 | * | 5/2002 |
|---|---|---|---|
| EP | 1208862 | * | 5/2002 |
| EP | 1208862 A1 | | 5/2002 |

* cited by examiner

*Primary Examiner*—Kevin C Sirmons
*Assistant Examiner*—Catherine N Witczak
(74) *Attorney, Agent, or Firm*—The Webb Law Firm; Mark Lindsey

(57) ABSTRACT

A shieldable collection needle assembly that shields the needle upon tube withdrawal includes a hub mounted on a needle cannula and a spring biased telescoping shield mounted on the hub. The needle assembly is matable with a needle holder adapted to receive the blood collection tubes. The needle assembly includes a retaining member moveably mounted on the hub and engageable with the telescoping shield when the collection tube is positioned in the needle holder. The retaining member prevents the telescoping shield from moving toward the fully extended position when engaged therewith. The telescoping shield will move toward the fully extended position when the retaining member is disengaged from the telescoping shield following removal of the collection tube from the needle holder.

34 Claims, 26 Drawing Sheets

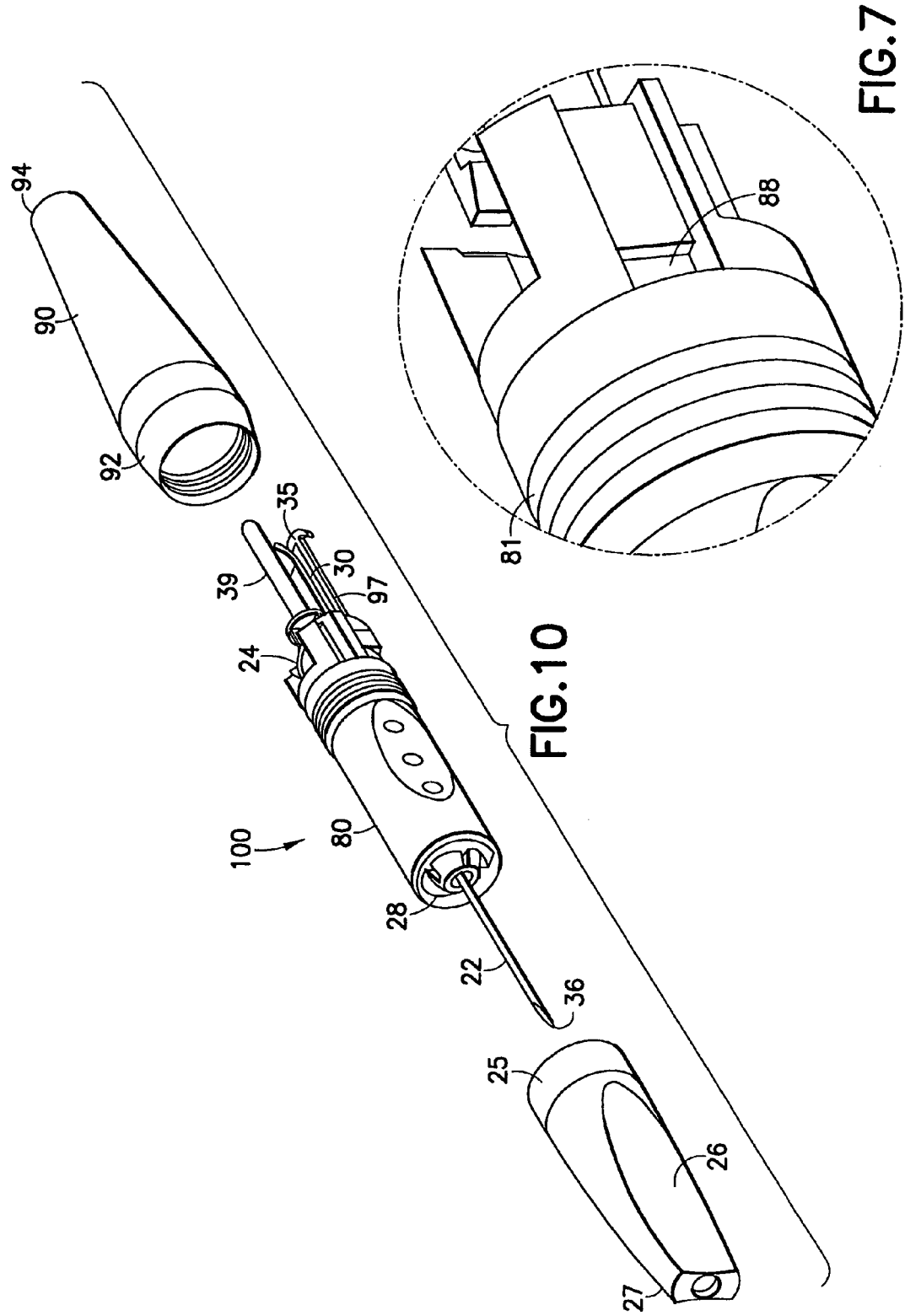

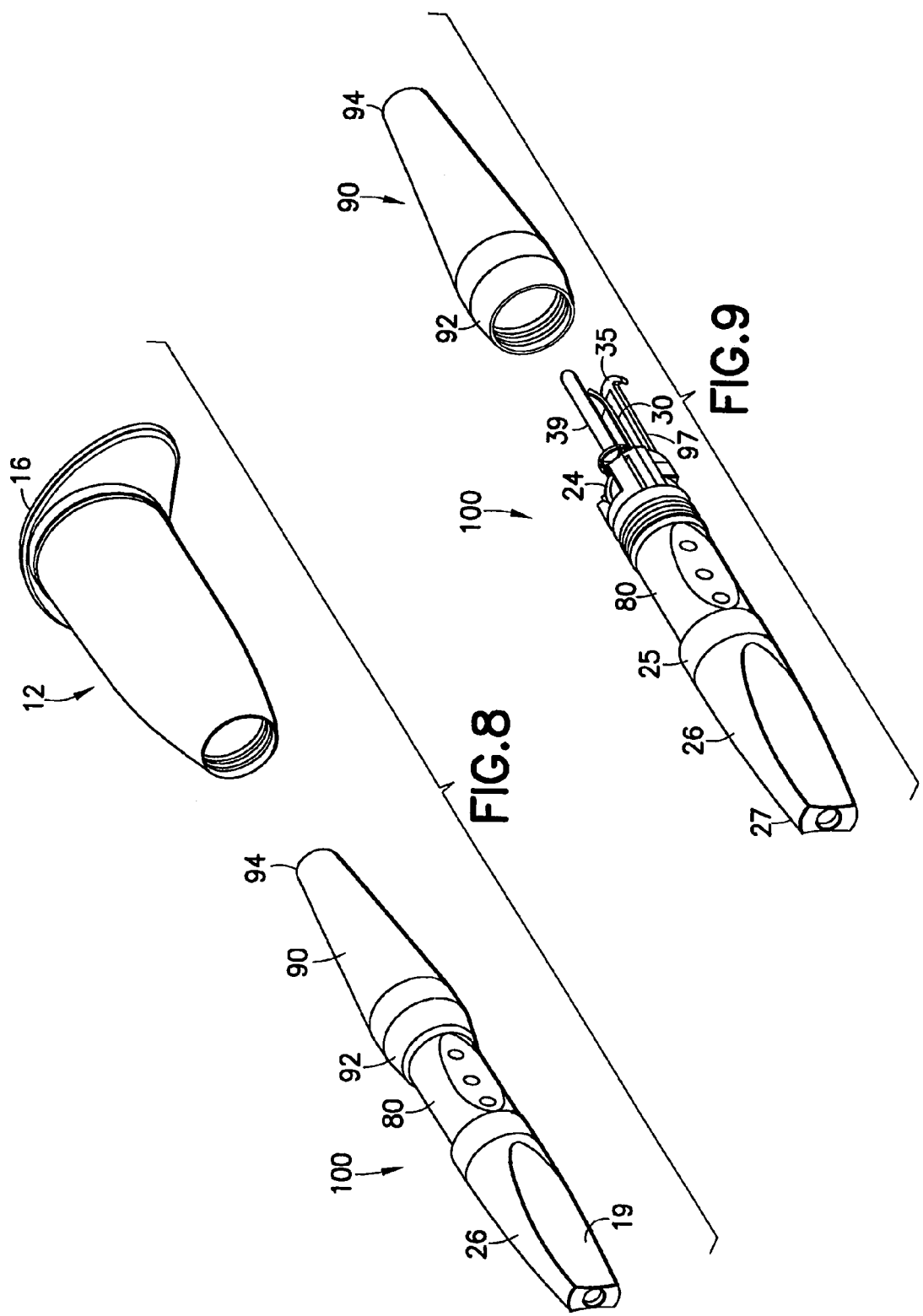

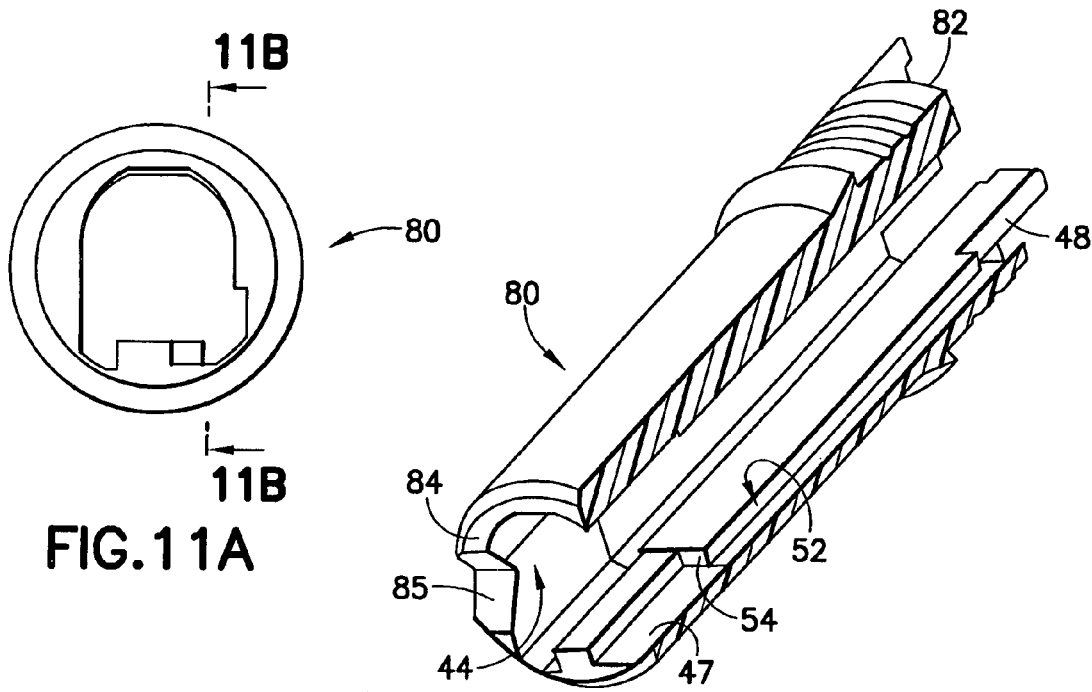
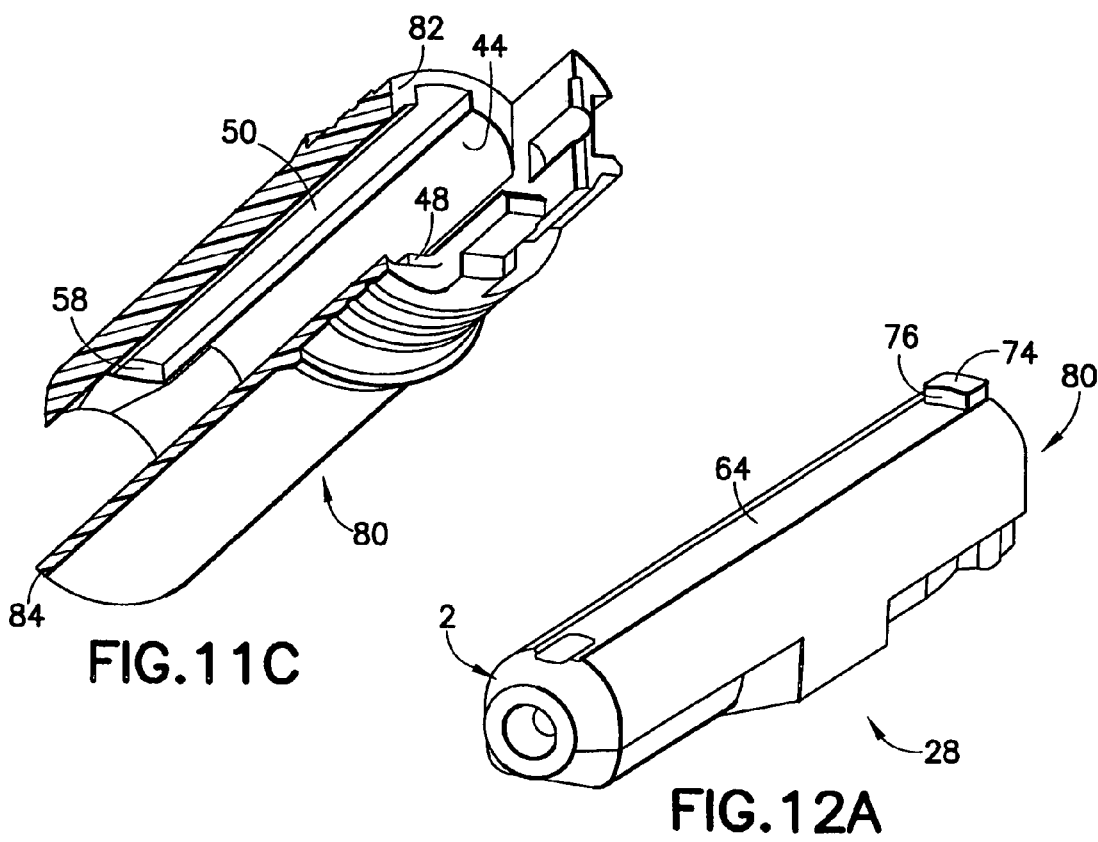

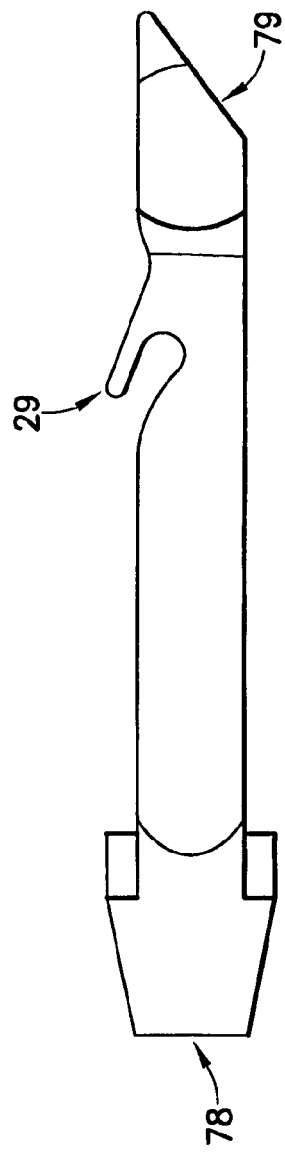
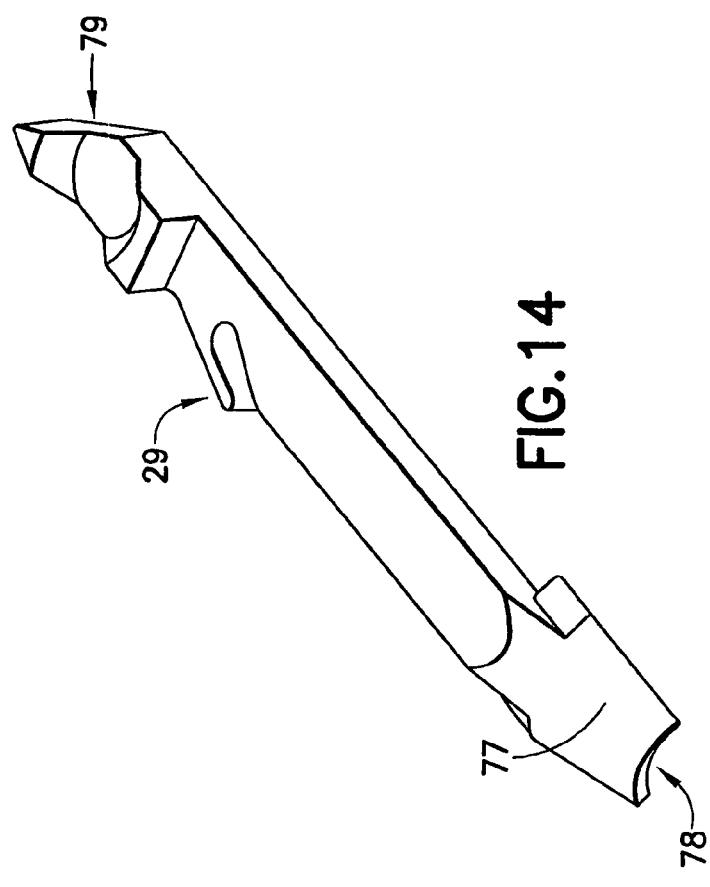
FIG.13
FIG.14

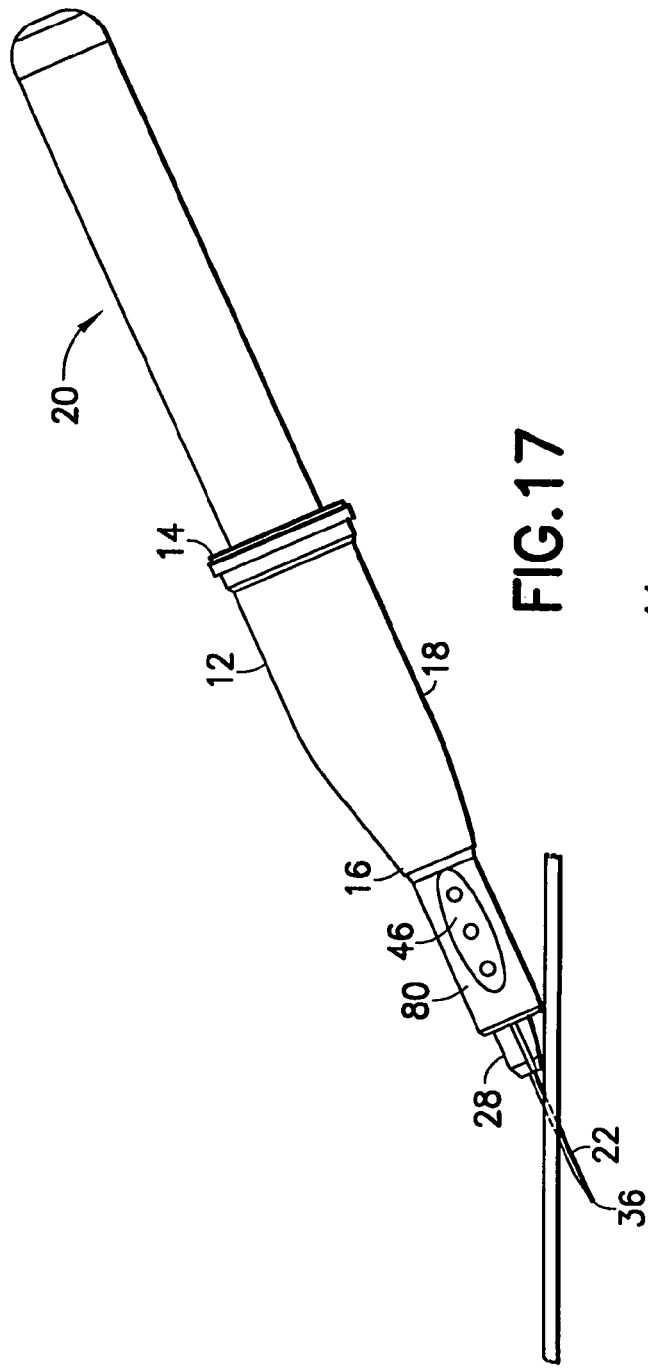
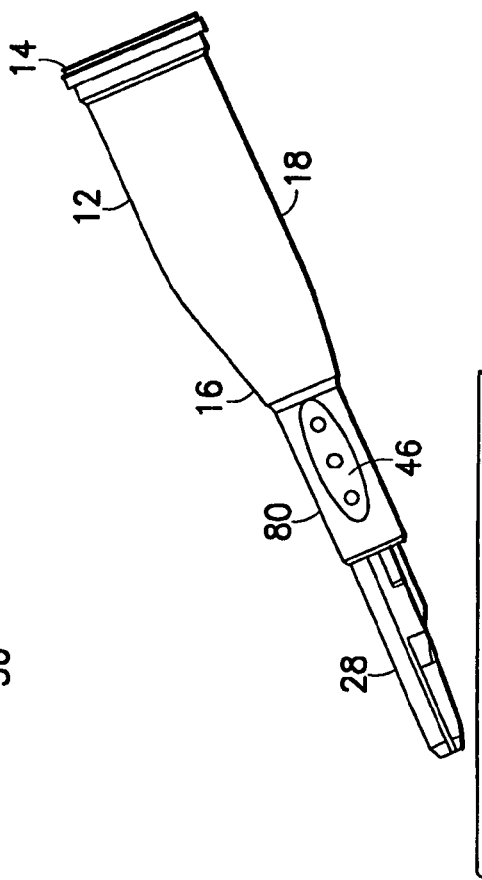
FIG.17
FIG.18

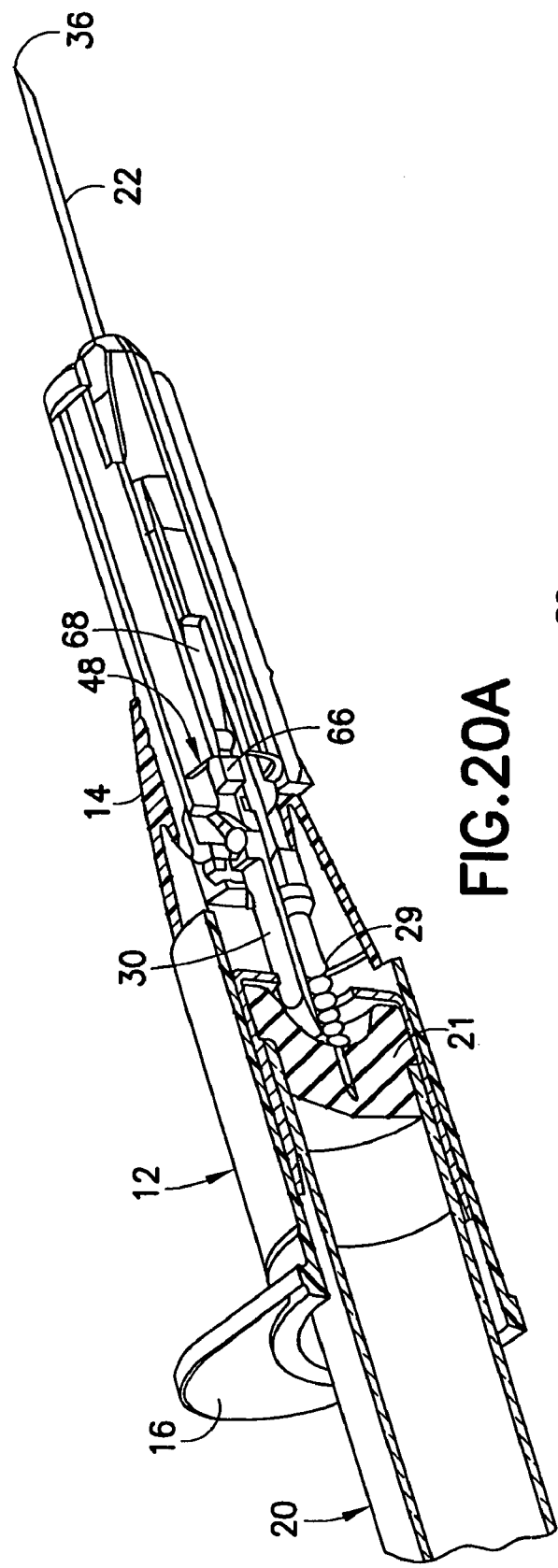
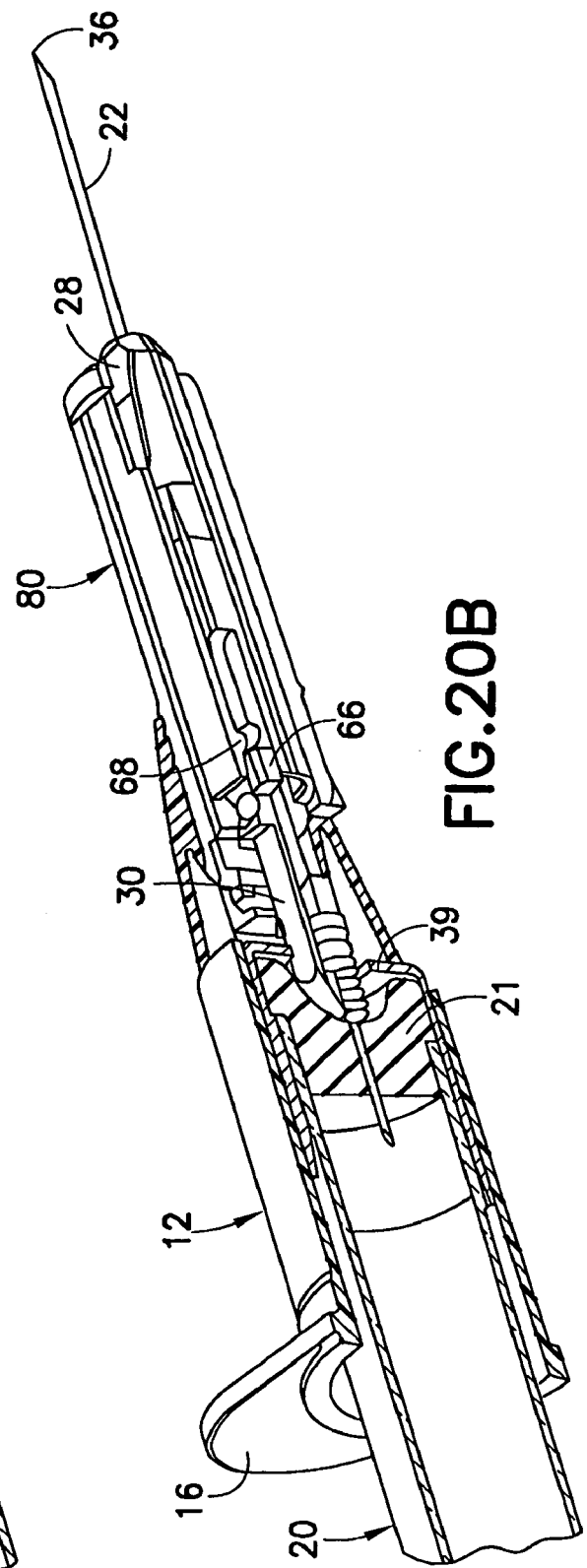
FIG. 20A
FIG. 20B

SAFETY SHIELDING NEEDLE ASSEMBLY WITH PASSIVE SHIELDING

RELATED APPLICATIONS

This application claims priority on U.S. Provisional Patent Appl. No. 60/463,384 filed Apr. 16, 2003.

BACKGROUND OF THE INVENTION

1. Field of the Invention

The present invention relates to a safety needle assembly with a telescoping shield that is activated during a standard sequence of operation of a medical procedure and, more particularly, relates to a needle and hub assembly having a telescoping shield that is activated when a sampling tube is removed from a needle holder.

2. Description of the Related Art

An evacuated collection tube, needle cannula (generally a double ended needle cannula) and needle holder are commonly used by a doctor, phlebotomist or nurse to draw a sample of body fluid from a patient in a hospital or doctor's office for diagnostic testing. During the use of such a collection needle assembly, the distal end of the needle cannula in the needle holder is inserted into the vein of the patient. The evacuated collection tube is then inserted into the proximal end of the needle holder until a needle (the proximal end of a double ended needle cannula) within the needle holder pierces a closure on the end of the tube. The vacuum in the tube then draws a body fluid sample from the patient through the needle cannula and into the tube. After the collection process is complete the needle cannula is removed from the vein and disposed of.

Because of the great concern that users of such needles may be contaminated with the blood of a patient by accidental sticks from the contaminated needle, it is preferable to cover the contaminated needle as soon as it is removed from the vein. For this reason, many developments have been made to provide means for covering the contaminated needle once it is removed from the patient. These devices usually involve some sort of shield arrangement that moves in place over the contaminated needle once it has been removed from the patient. However, these shield arrangements have required the use of one or two hands to perform the operation of moving the shield over the contaminated needle, which is a hindrance to the user.

Alternatively, needles with internal or external blunting cannulas have been used that extend from the needle to blunt the distal end. However, these devices require an additional manual operation to drive the blunting cannula over or out of the needle upon completion of blood drawing to protect the user from the sharp end of the needle and also allow the user to draw blood without triggering the safety device. Such devices also require the internal diameter of the needle to be decreased, which may affect blood flow or require the external diameter of the needle to be enlarged and may cause unnecessary discomfort to the patient.

Other needles have shields that are activated during the venipuncture operation when the shield comes in contact with the skin. Using the skin to activate the device is not desirable since the device may not activate if the needle does not penetrate sufficiently or may cause the shield to inadvertently lock when probing for the vein. Such devices may also require excessive penetration into some patients to cause the triggering means to activate the device, which will cause a phlebotomist to unnecessarily have to change their standard method or procedure.

U.S. Pat. Nos. 5,718,239 and 5,893,845, which are incorporated herein by reference, provide safety needle assemblies incorporating a telescoping shield that extends over the distal end of the needle cannula when released by an actuator that is triggered during a standard sequence of operation of a medical procedure. In particular, when the closure or stopper on the collection tube compresses a rubber multiple sample sleeve on the proximal end of the needle cannula, an actuator is triggered by the closure and/or sleeve to cause the telescoping shield to extend to contact the skin of a patient. Then, when the needle end of the cannula is removed from the patient, the telescoping shield continues to extend to a fully extended and locked position over the distal end of the needle cannula, thereby rendering the needle assembly safe and preventing needle stick injuries.

Although providing significant improvements over the prior art systems, the system of the '239 and '845 patents involving deployment of the telescoping sleeve upon tube insertion can be a distraction to the user, in the event they must probe for the vein after shield is activated. There is a need, therefore, for a safety shielding needle mechanism that does not require manipulation beyond that which is familiar to medical technicians with the use of conventional blood collection needles and which is deployed following the withdrawal of the tube from the needle holder.

An object of the present invention is to provide a needle shield that is automatically activated during the normal procedure used during blood collection. It is a further object of the present invention to provide a needle assembly shielding mechanism that is activated upon insertion of an evacuated tube into the needle holder and deployed upon withdrawal of the tube from the needle holder.

SUMMARY OF THE INVENTION

The above problems with the prior art are addressed with a passively shielded needle assembly according to the present invention. The present invention includes a needle cannula, such as a double ended needle cannula, having a proximal end and a distal end with a hub mounted to the needle cannula at a location spaced from the distal end. The invention includes a telescoping shield slidably mounted on the hub and moveable between a fully retracted position and a fully extended position encapsulating the distal end of the needle cannula. A first biasing member, such as a spring, may be mounted on the hub and bias the telescoping shield towards the fully extended position. The hub may include a releasable lock for initially holding the telescoping shield in the fully retracted position. An actuator may be moveably mounted on the hub for releasing the lock, wherein the actuator is activated by pressure applied during a standard sequence of operation of a medical device, such as insertion of an evacuated tube into a needle holder that is coupled to the hub. Significantly, the invention includes a retaining member moveably mounted on the hub and releasably engageable with the telescoping shield, wherein the retaining member holds the telescoping shield from moving toward the fully extended position when engaged therewith. The telescoping shield will move toward the fully extended position when the actuator has released the lock and the retaining member is disengaged from the telescoping shield, such as upon removal of an evacuated tube from the needle holder.

In one embodiment of the invention, the actuator may include at least one actuating arm slidably mounted on the hub for releasing the lock. Further, the lock may include at least one locking recess and the telescoping shield may include a corresponding locking lug, wherein each locking recess is engageable with a corresponding locking lug, and wherein the actuating arm disengages each locking lug from the corresponding locking recess to release the lock. The retaining member may include at least one retaining arm slidably mounted on the hub, wherein the retaining member engages at least one locking lug after the actuating arm has disengaged the locking lug from the locking recess.

The invention may include a biasing member biasing the retaining member away from engagement with the telescoping shield. Further, this biasing member may be positioned to be prevented from moving the retaining member away from engagement with the telescoping shield for a period of time following when the actuator is activated by pressure applied during the standard sequence of operation of the medical device. For example, the biasing member may be prevented from moving the retaining member out of engagement with the telescoping sleeve until the evacuated tube is removed from the needle holder.

The invention may further include a second lock, such as a cannula lock or a locking engagement between the telescoping shield and the hub, for securing the telescoping shield in the fully extended position. The invention may further include a manual shield activation to allow the operator to manually deploy the shield if desired and supplement the automatic passive deployment features.

The present invention provides a method of passively shielding a needle assembly including the steps of: providing and mounting a needle holder on the hub; inserting an evacuated tube onto the needle holder; engaging the telescoping shield with the retaining member upon insertion of the evacuated tube to prevent the telescoping shield from moving to a needle cannula encapsulating position; removing the evacuated tube from the needle holder; disengaging the retaining member from the telescoping shield with the removal of the evacuated tube; and moving the telescoping shield toward the needle cannula encapsulating position with the removal of the evacuated tube from the needle holder.

These and other objects and further advantages of the invention will be more readily understood upon consideration of the following detailed description and the accompanying drawings.

BRIEF DESCRIPTION OF THE DRAWINGS

FIG. 7 is an enlarged view of a portion of FIG. 6;

FIG. 8 is an exploded perspective view of a needle assembly with a detached holder according to the present invention;

FIG. 9 is an exploded perspective view of the needle assembly of FIG. 8 with a non-patient shield detached;

FIG. 10 is an exploded perspective view of the needle assembly of FIG. 8 with the packaging and non-patient shield detached;

FIG. 11A is a front view of the housing of the present invention;

FIG. 11B is a perspective sectional view of the housing of FIG. 11A taken along line 11B, 11C-11B, 11C in FIG. 11A;

FIG. 11C is a perspective sectional view of the housing of FIG. 11A taken along line 11B, 11C-11B, 11C in FIG. 11A;

FIG. 12A and 12B are perspective and side elevational views, respectively, of a safety needle shield of the present invention;

FIG. 13 is an elevational view of the actuator of the present invention;

FIG. 14 is a perspective view of an actuator of the present invention;

FIG. 17 is a side elevational view of the needle assembly prior to shielding;

FIG. 18 is a side elevational view of the needle assembly after shielding;

FIG. 20A is a perspective sectional view of the present invention before actuator safety shield release;

FIG. 20B is a perspective sectional view of the present invention during actuator safety shield release during engagement of the retaining member;

DETAILED DESCRIPTION OF THE PREFERRED EMBODIMENTS

The needle assembly 10 of the present invention is shown in FIGS. 1-7 and 11-20. It will be noted that the term "distal" as used herein refers to the end of the needle assembly that punctures the patient's skin while "proximal" means the end of the needle assembly that punctures an evacuated container.

Figure 1:
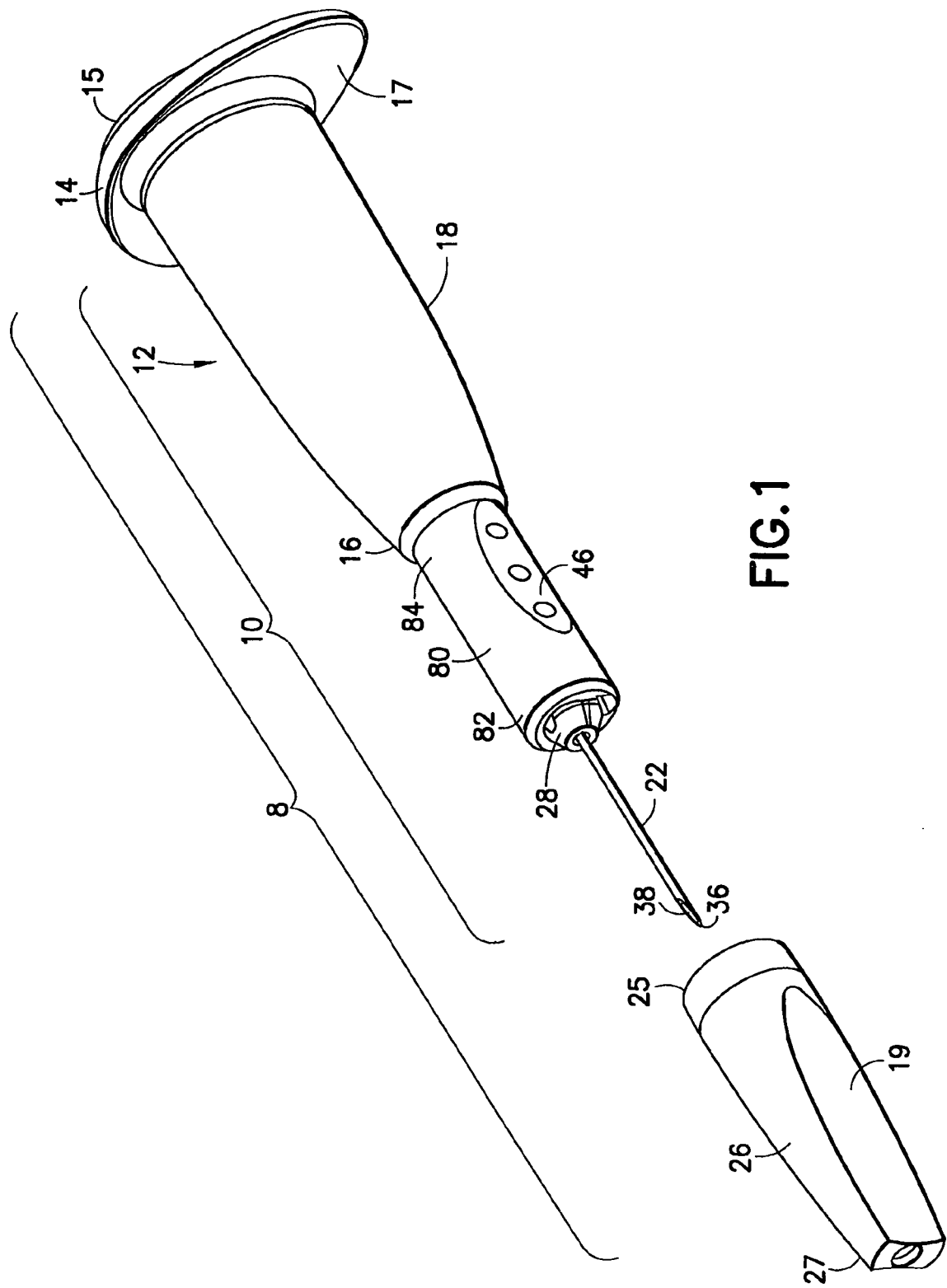
FIG. 1 is a perspective view of a needle assembly according to the present invention.
Figure 2:
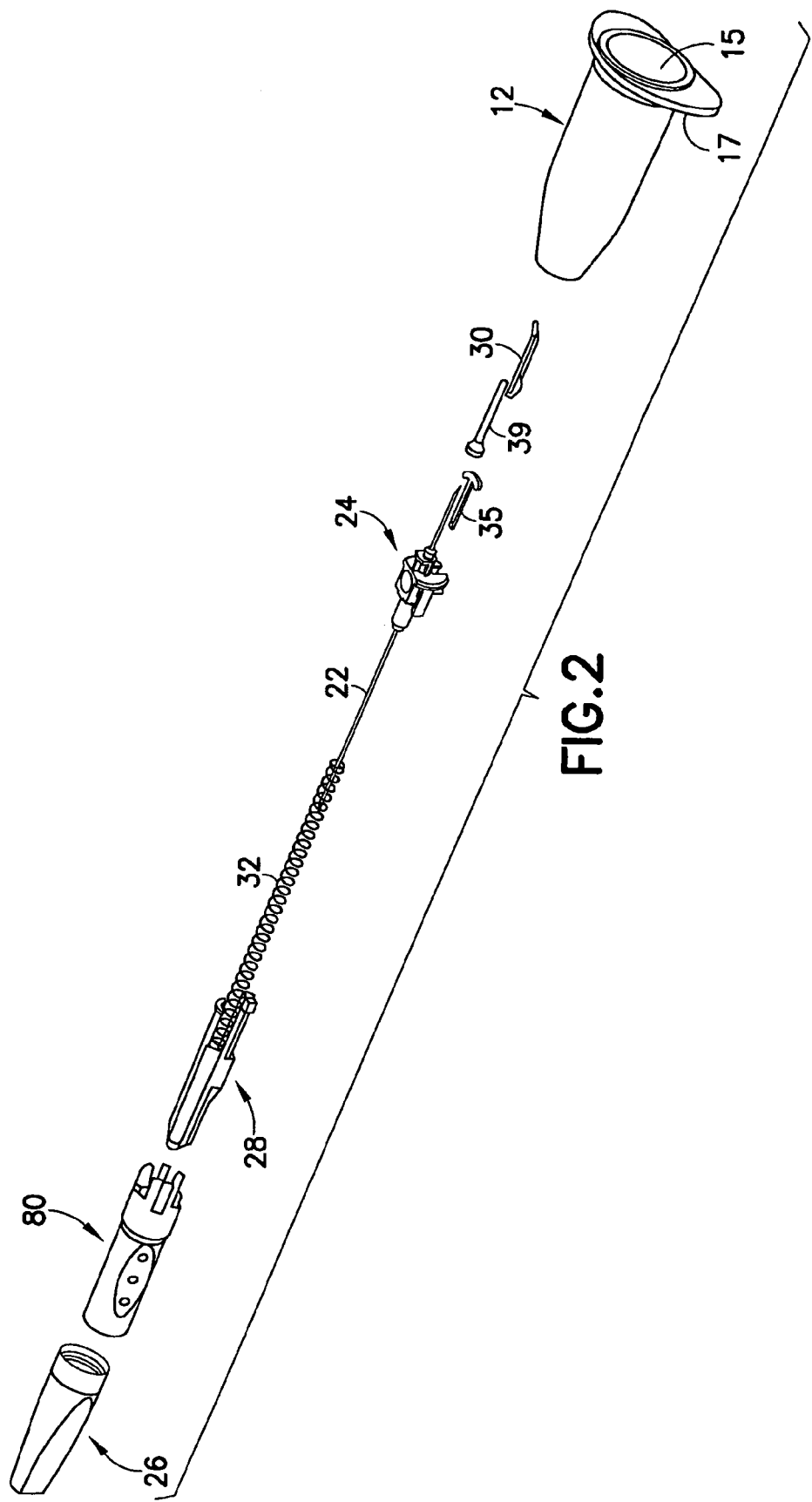
FIG. 2 is an exploded perspective view of the needle assembly shown in FIG. 1.
Figure 3:
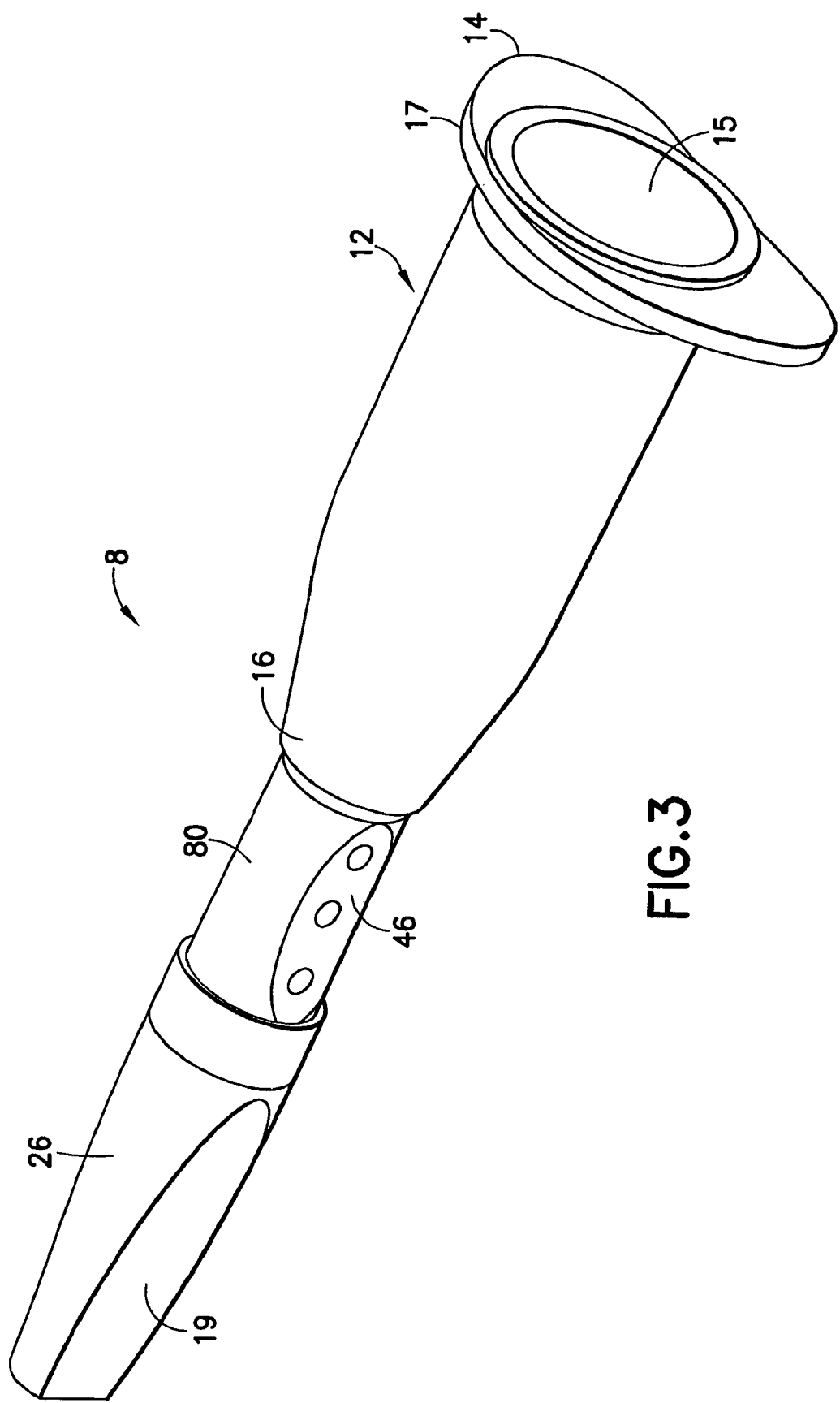
FIG. 3 is a perspective view of the needle and holder assembly shown in FIG. 2 with a packaging shield covering the needle cannula before use.
Figure 4:
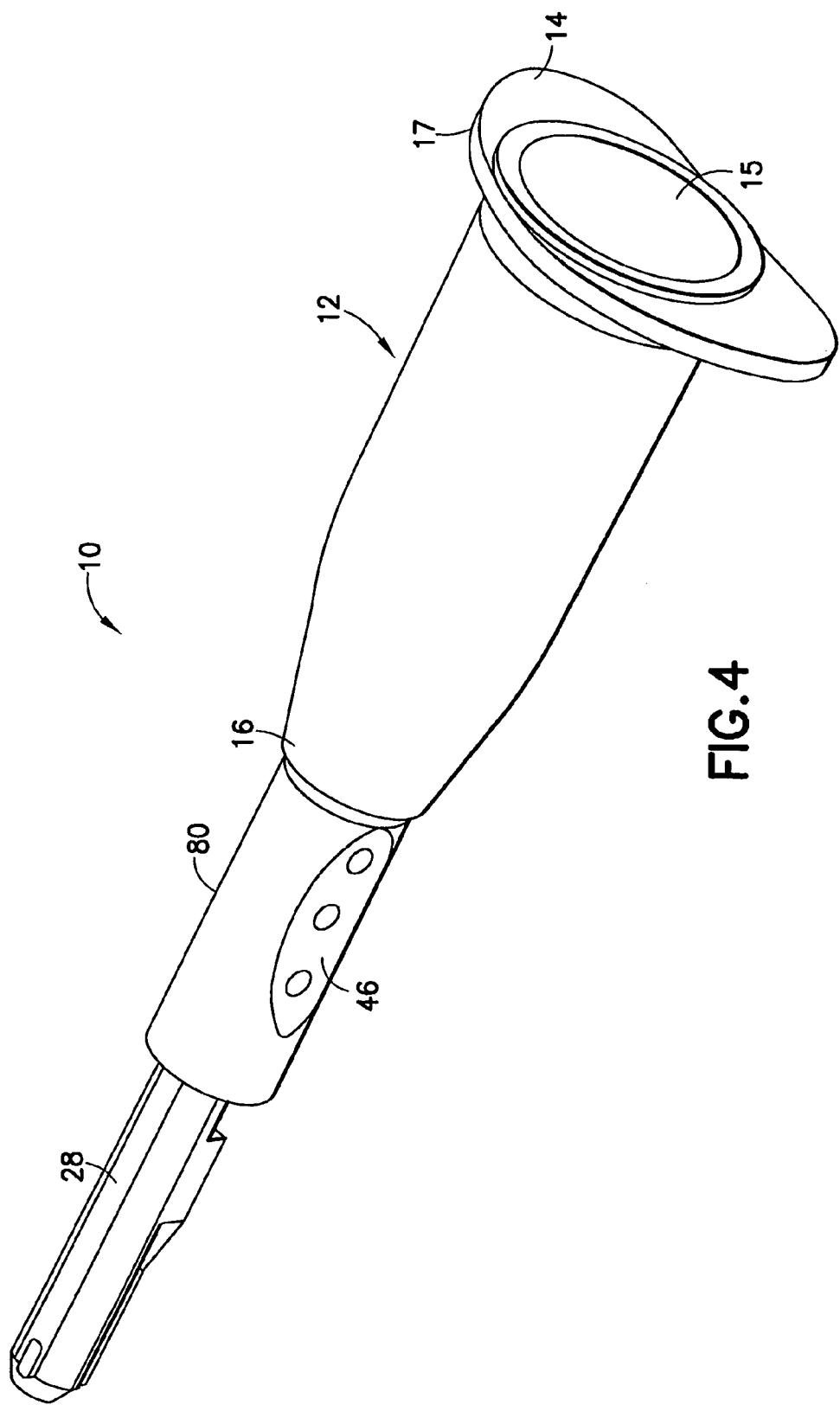
FIG. 4 is a perspective view of the needle assembly of FIG. 1 with a needle shield covering the needle cannula after use.
Figure 19A:
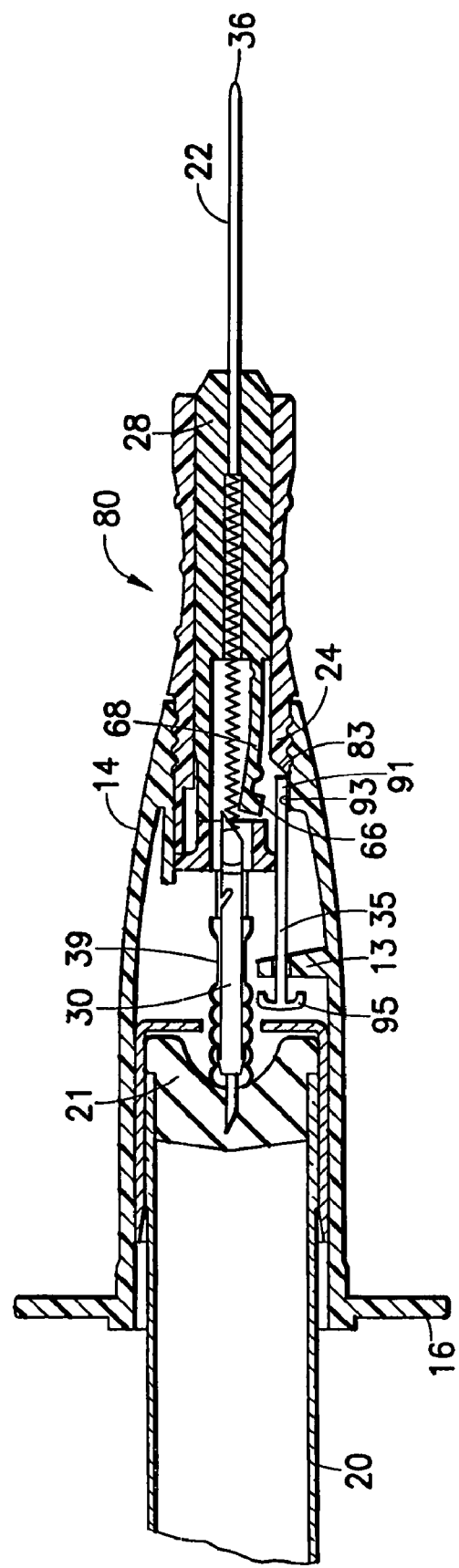
FIG. 19A is a sectional view of the present invention before actuator safety shield release.
Figure 19B:
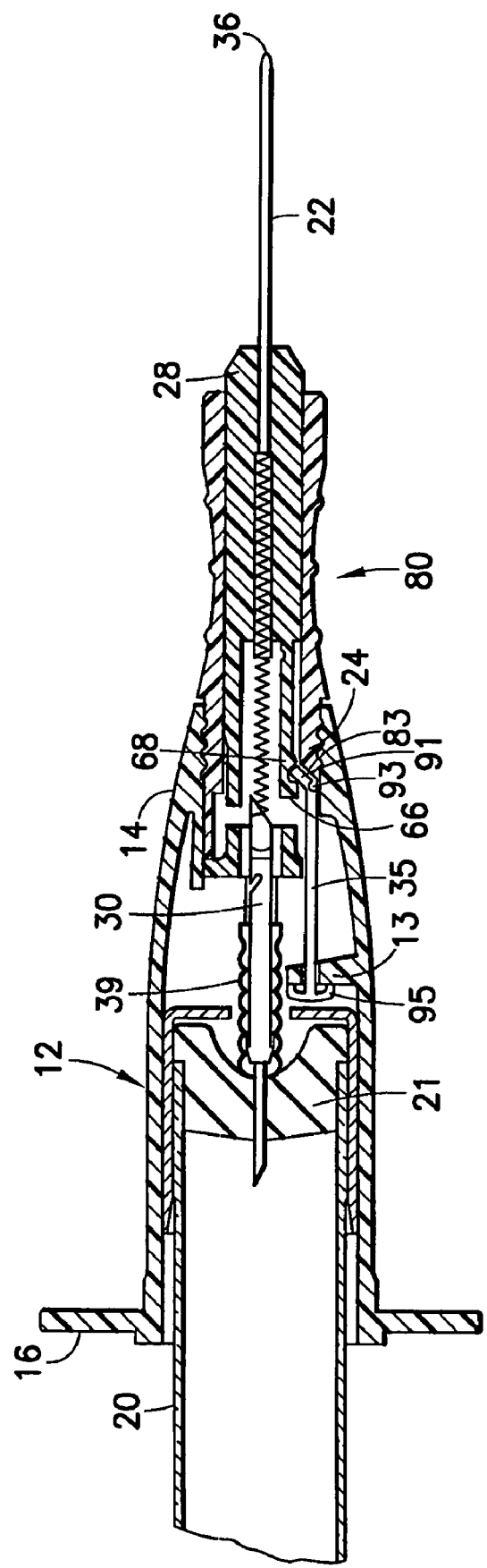
FIG. 19B is a sectional view of the present invention during actuator safety shield release with engagement of the retaining member.
Figure 19C:
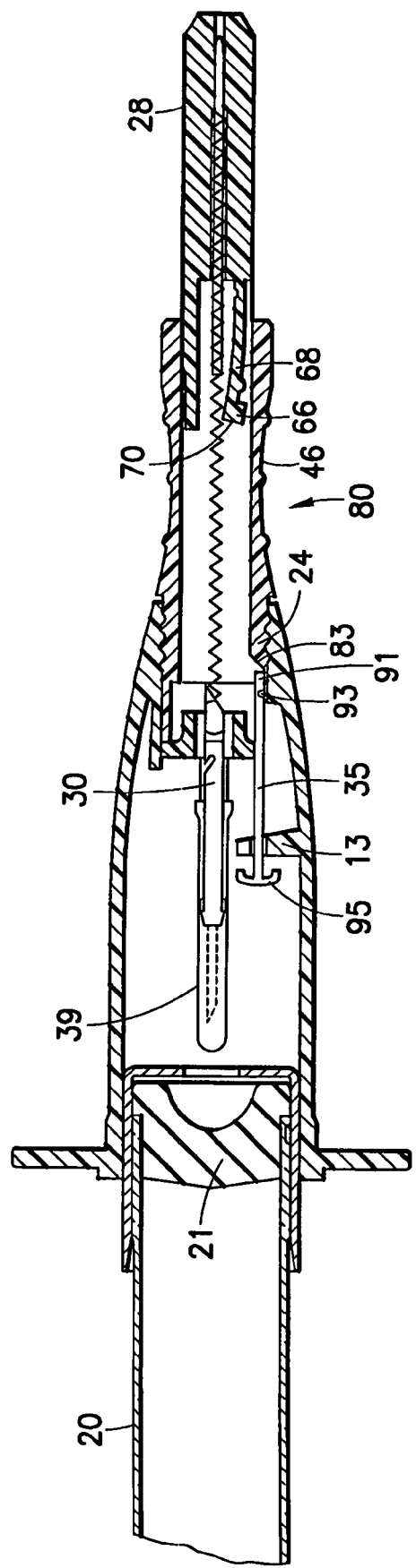
FIG. 19C is a sectional view of the present invention after actuator safety shield release and disengagement of the retaining member where the shield is covering the distal end of the needle cannula.
Figure 20C:
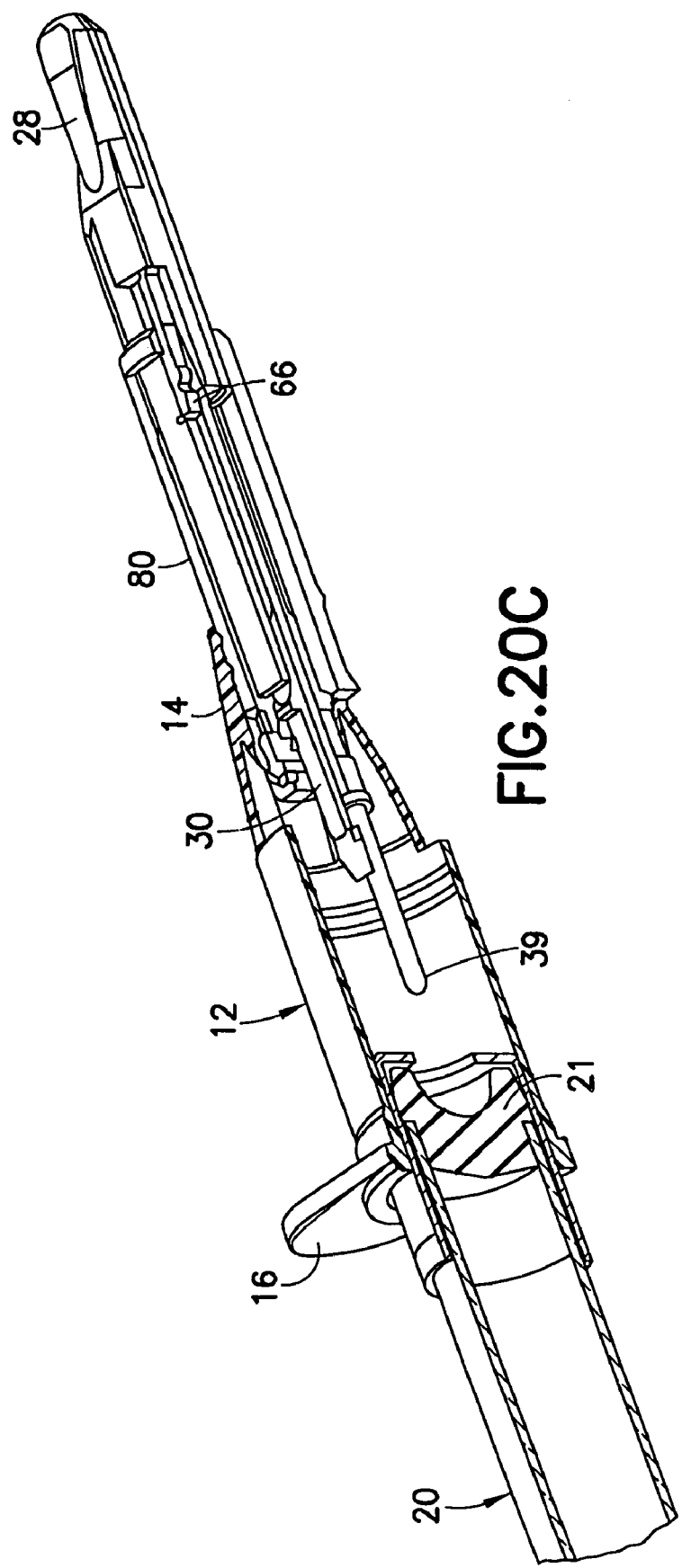
FIG. 20C is a perspective sectional view of the present invention after actuator safety shield release and disengagement of the retaining member where the shield is covering the distal end of the needle cannula.
Figure 21:
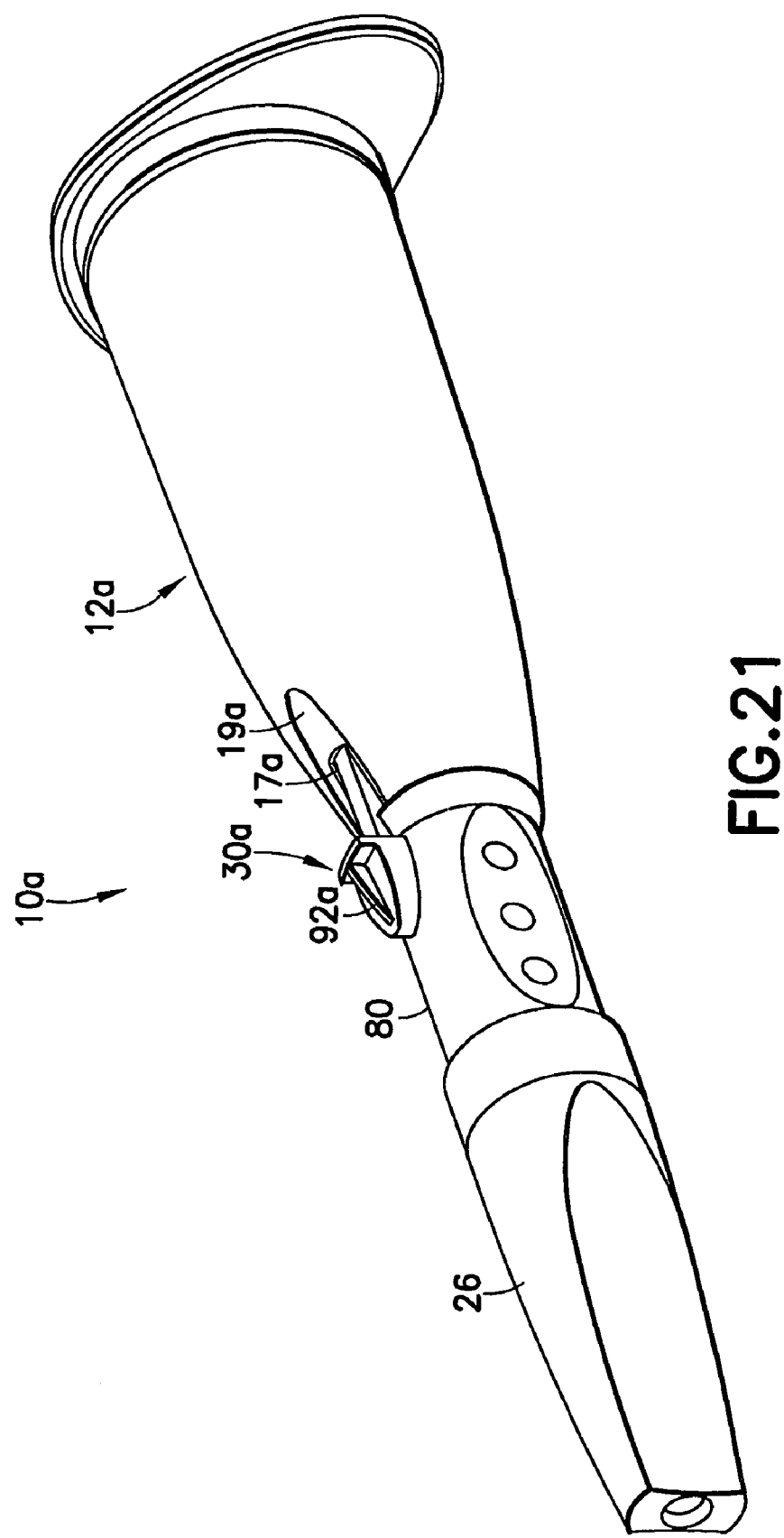
FIG. 21 is a perspective view of another embodiment of the present invention.
Figure 22:
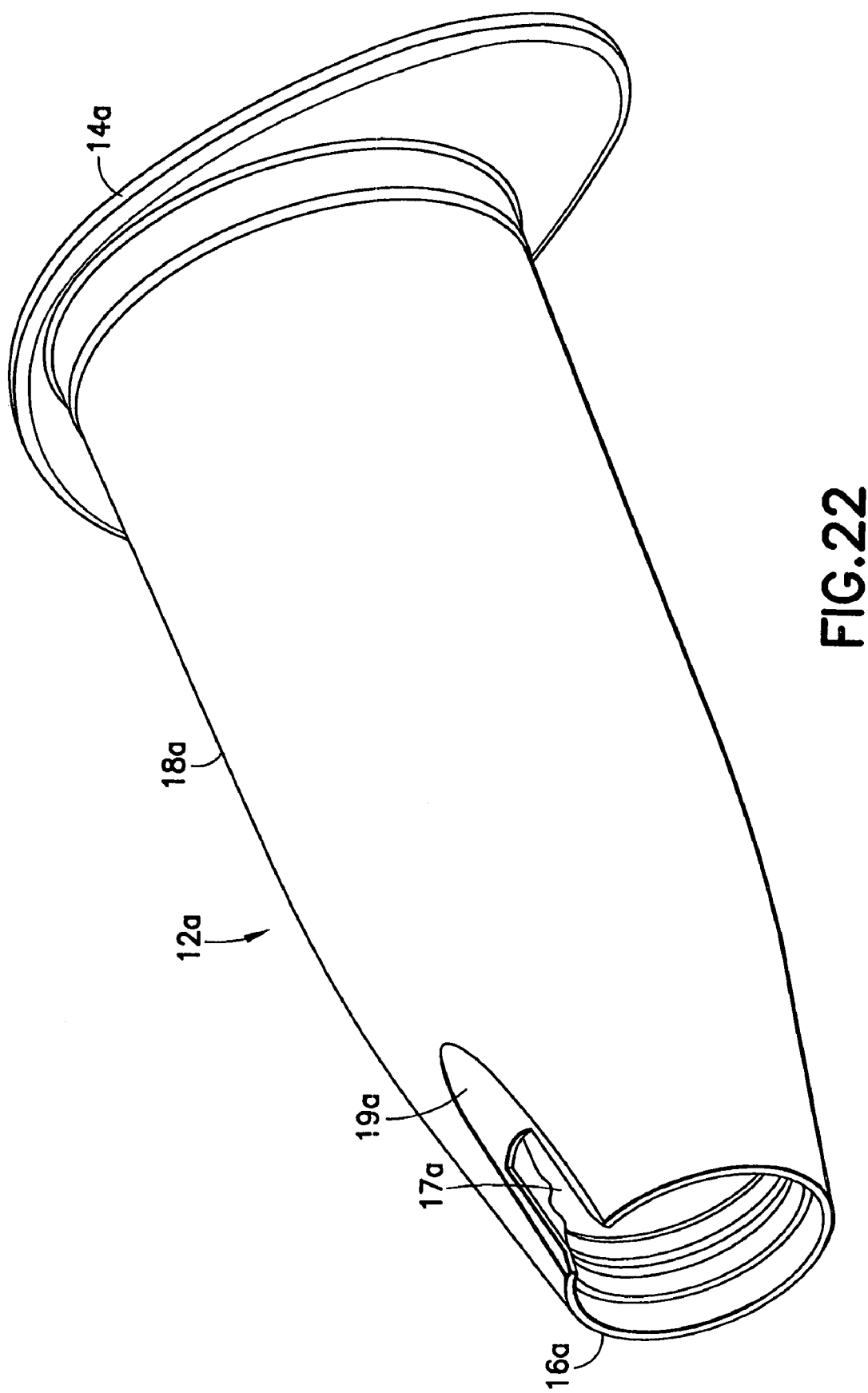
FIG. 22 is a perspective view of a holder for use with the embodiment of FIG. 21.
Figure 23:
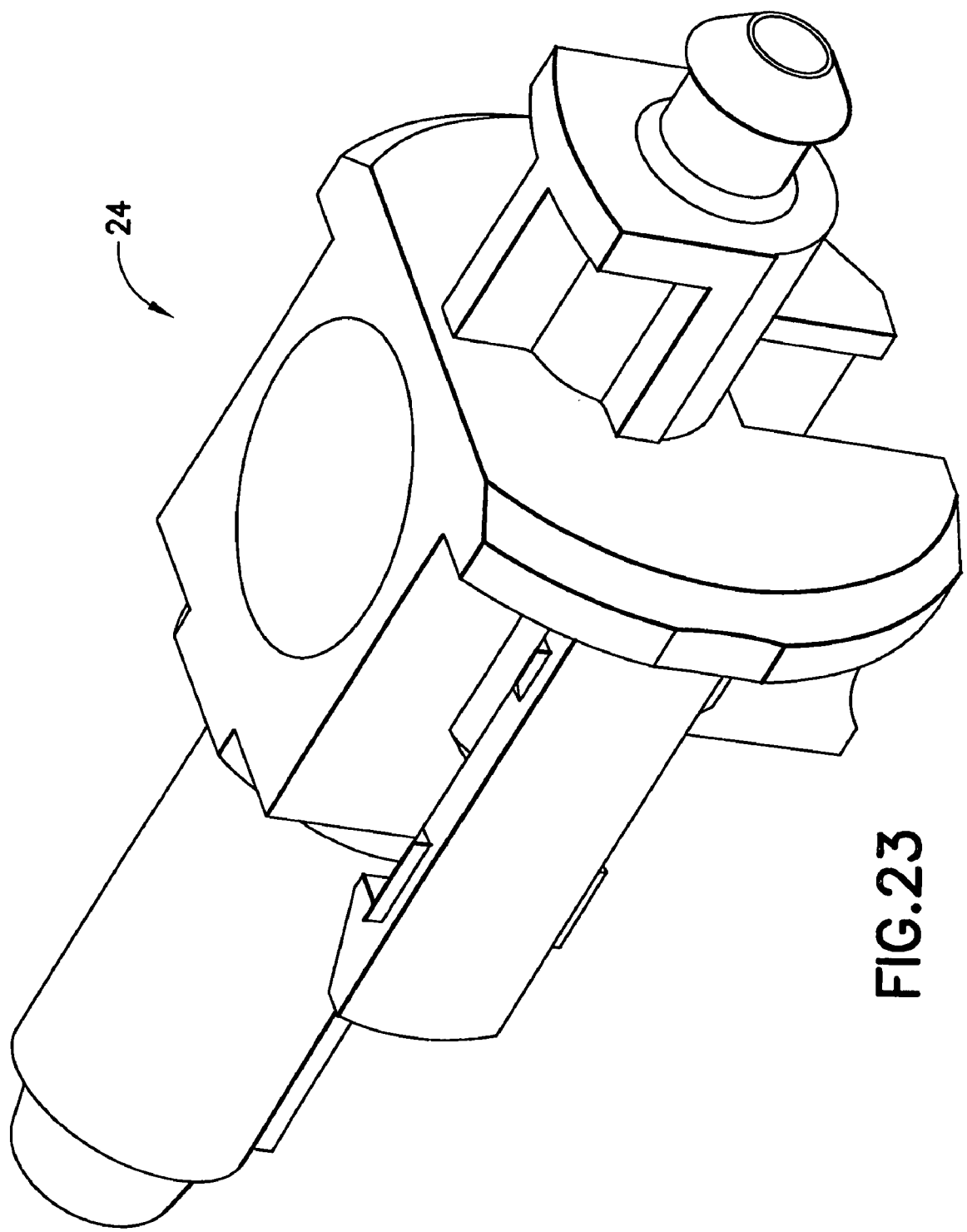
FIG. 23 is a perspective view of a hub for use with the embodiment of FIG. 21.
Figure 24:
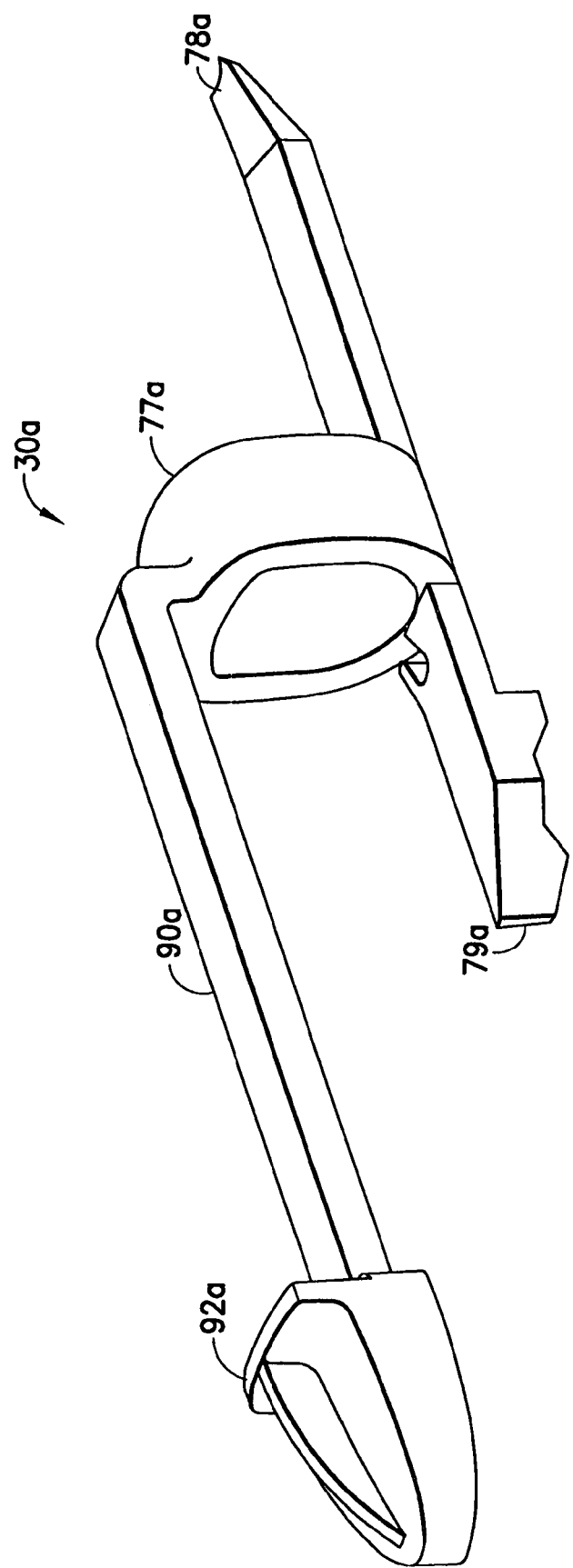
FIG. 24 is a perspective view of an actuator for use with the embodiment of FIG. 21.
Figure 25:
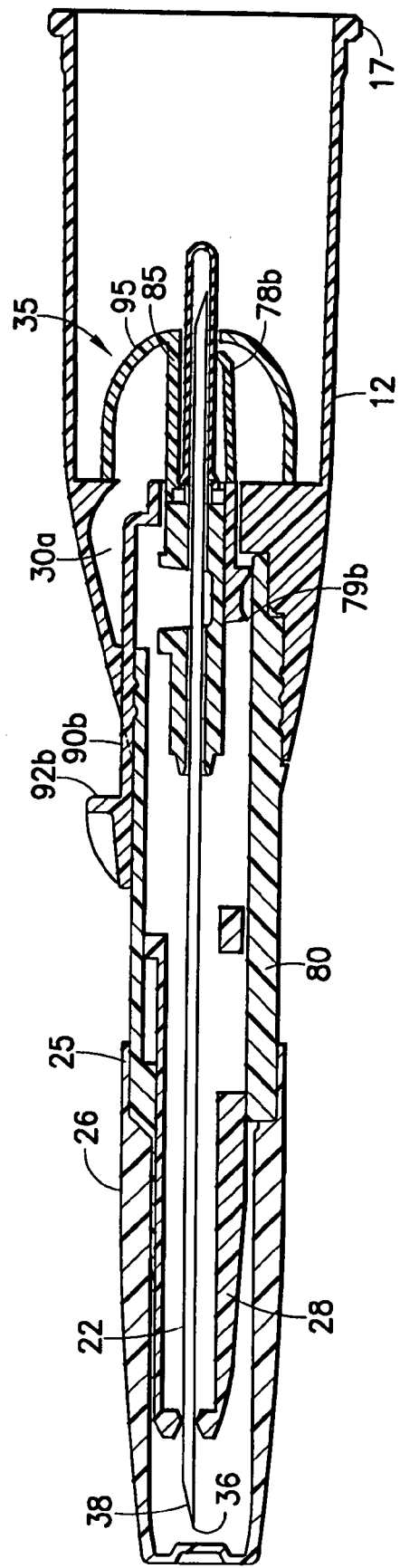
FIG. 25 is a sectional view of the needle assembly shown in FIG. 21.
Figure 26A:
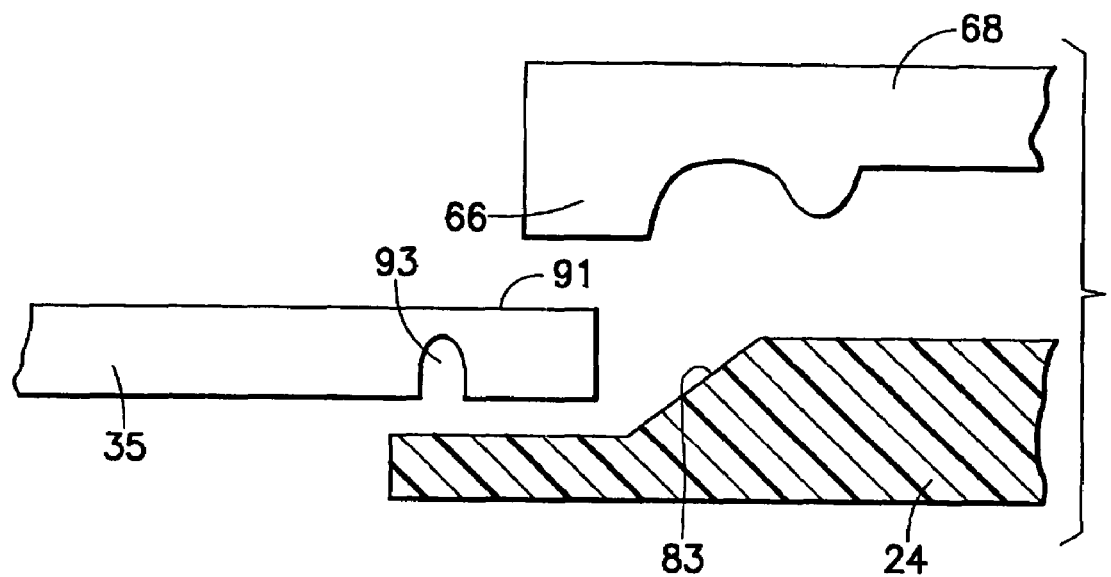
FIGS. 26A and 26B are enlarged schematic views illustrating the engagement of the retaining member and the safety shield in the embodiment of FIGS. 19A-19C.
Figure 26B:
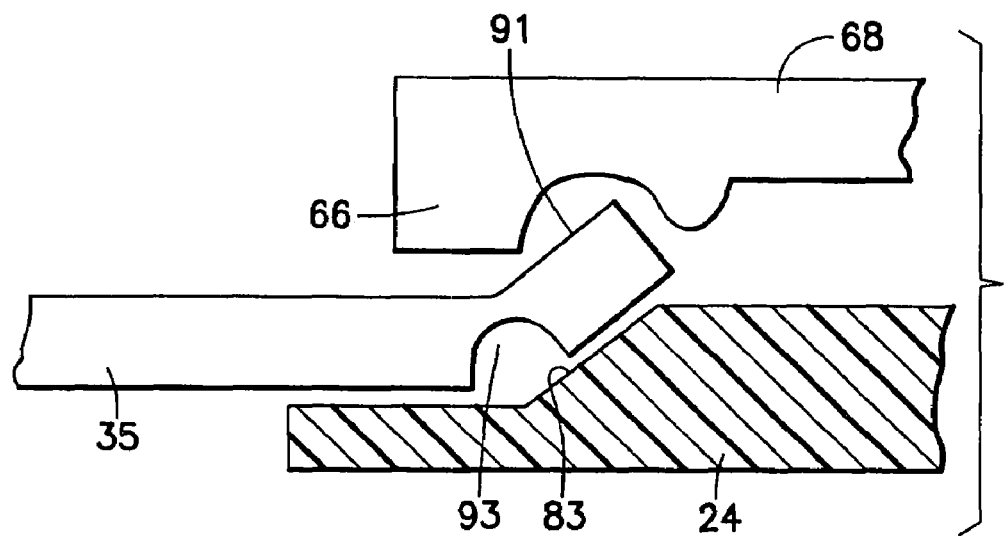

Needle assembly 10 is mounted to a needle holder 12, as shown in FIGS. 1,3, and 4. Needle holder 12 has a proximal end 14, a distal end 16 and a tubular sidewall 18 extending between ends 14 and 16. Proximal end 14 of needle holder 12 is open and is adapted to receive a blood collection tube 20 as shown in FIGS. 17, 19A-19C, and 20A-20C. FIGS. 20A-20C omit the retaining member for clarity. However, proximal end 14 of holder 12 may have a removable seal or cap 15 for sterility. Proximal end 14 of holder 12 also has a radially aligned finger flange 17 to facilitate manipulation of holder 12. Flange 17 is a non-circular to prevent holder 12 from rolling. Flange 17 preferably has a linear edge to provide a clear indication of the top and bottom sides. Distal end 16 of needle holder 12 includes structure to which needle assembly 10 is mounted. In particular, distal end 16 of needle holder 12 may be formed with non-threaded mounting means, such that needle holder 12 is substantially fixed to needle assembly 10 after assembly. The non-threaded mounting means comprises a combination of external rings 81 and keyways to secure needle assembly 10 axially and circumferentially. It is preferred that needle assembly 10 is mounted to needle holder 12 by the manufacturer so that the device is ready for fast and convenient use. Most importantly, pre-assembled needle assemblies 10 and needle holders 12 ensure that the proximal point of the needle is enclosed within holder 12 before, during, and after blood collection. Alternately, however, the distal end of the needle holder may be formed with an internal array of threads that are engageable by external threads on the needle assembly.

Needle assembly 10 ideally is packaged in a blister package having a thermoformed blister and top web. The top web is comprised of a material that may be permeable to gas such as ethylene oxide gas. Optionally, the proximal end 14 of the holder 12 can be covered with a paper-like membrane that is thermally or adhesively sealed onto the proximal end 14 of the holder. Examples of materials used for a paper-like membrane are Tyvek® manufactured by DuPont, and examples of materials to be used for a thermoformed blister package include glycol modified polyethylene terephthalate (PETG), polyethylene terephthalate (PET), high-density polyethylene, polypropylene, polycarbonate, nylon, and K-resin. In the configuration with a paper-like membrane covering the open proximal end 14 of holder 12, a thermoformed blister and top web would not be required, and the entire assembly can be sterilized by ethylene oxide gas or cobalt 60 irradiation.

Needle assembly 10 includes a needle cannula 22, a needle hub 24, a packaging shield 26, a safety shield 28, a sleeve 39, a housing 80, an actuator 30, a releasable retaining member 35, and a spring 32. In other embodiments, a portion of the needle assembly (e.g., the housing 80) can be integral or unitary with the needle holder or hub to reduce assembly steps by the manufacturer and the user.

Figure 5:
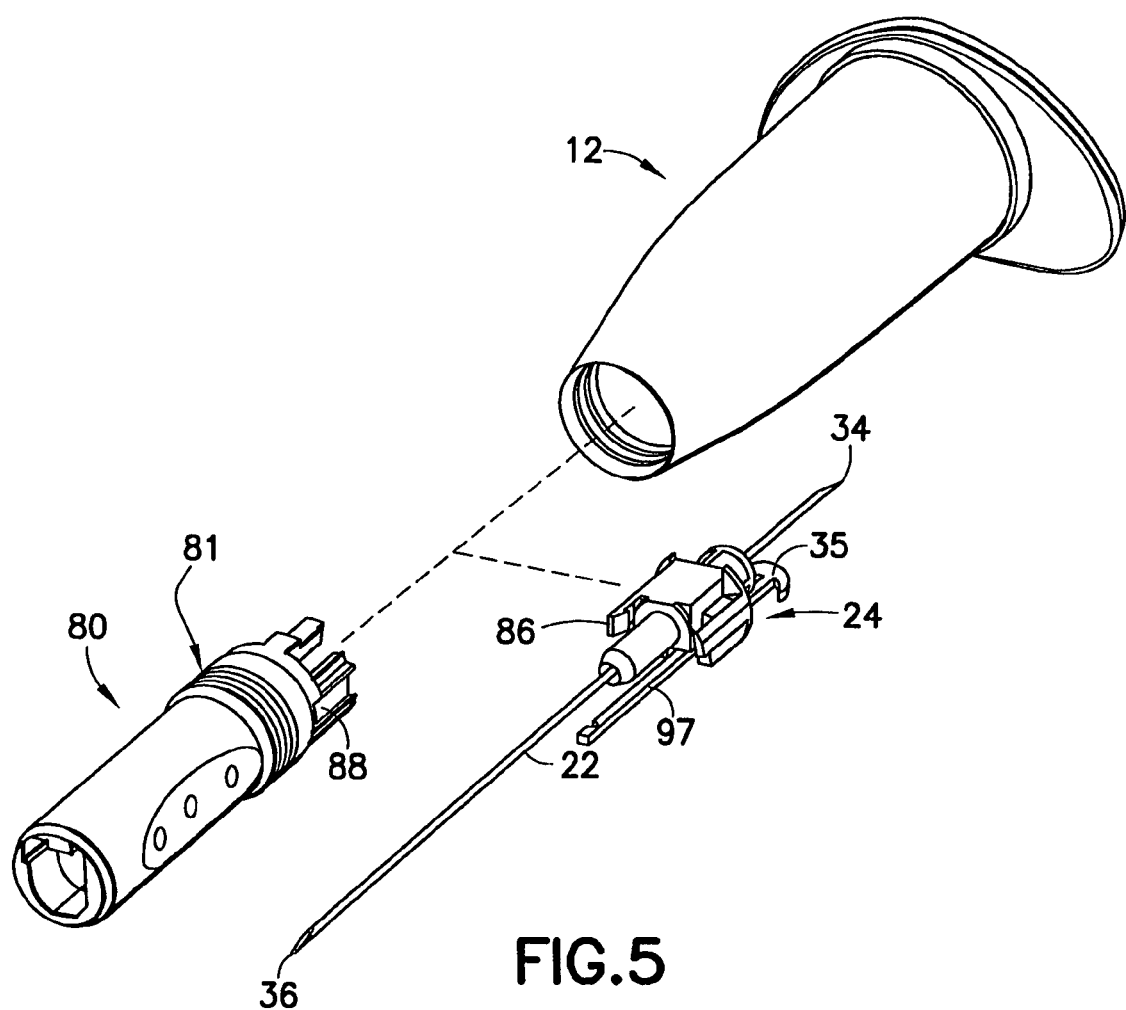
FIG. 5 is an exploded perspective view of the cannula, a hub sub-assembly, housing and holder sub-assembly.
Figure 6:
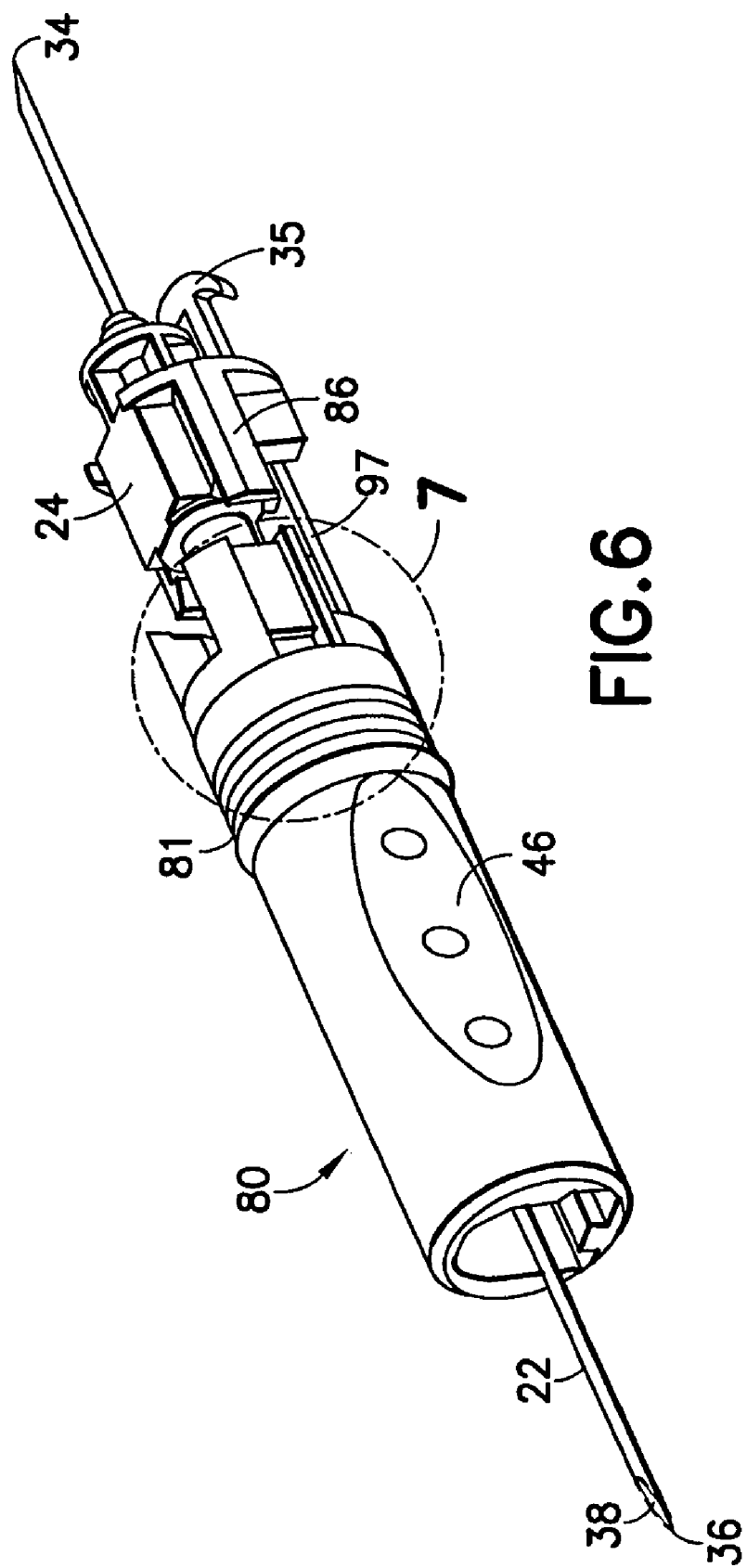
FIG. 6 is a partially exploded view of the cannula and the hub sub-assembly and housing.

Needle cannula 22 includes a pointed proximal end 34, as shown in FIGS. 1, 5, and 6, a sharply beveled distal end 36 and a lumen 38 extending therebetween. Proximal end 34 of needle cannula 22 is covered by an elastomeric multiple sample sleeve 39 (shown in FIGS. 2, 9, and 10) that can be pierced by pointed proximal end 34 of needle cannula 22.

Figure 15:
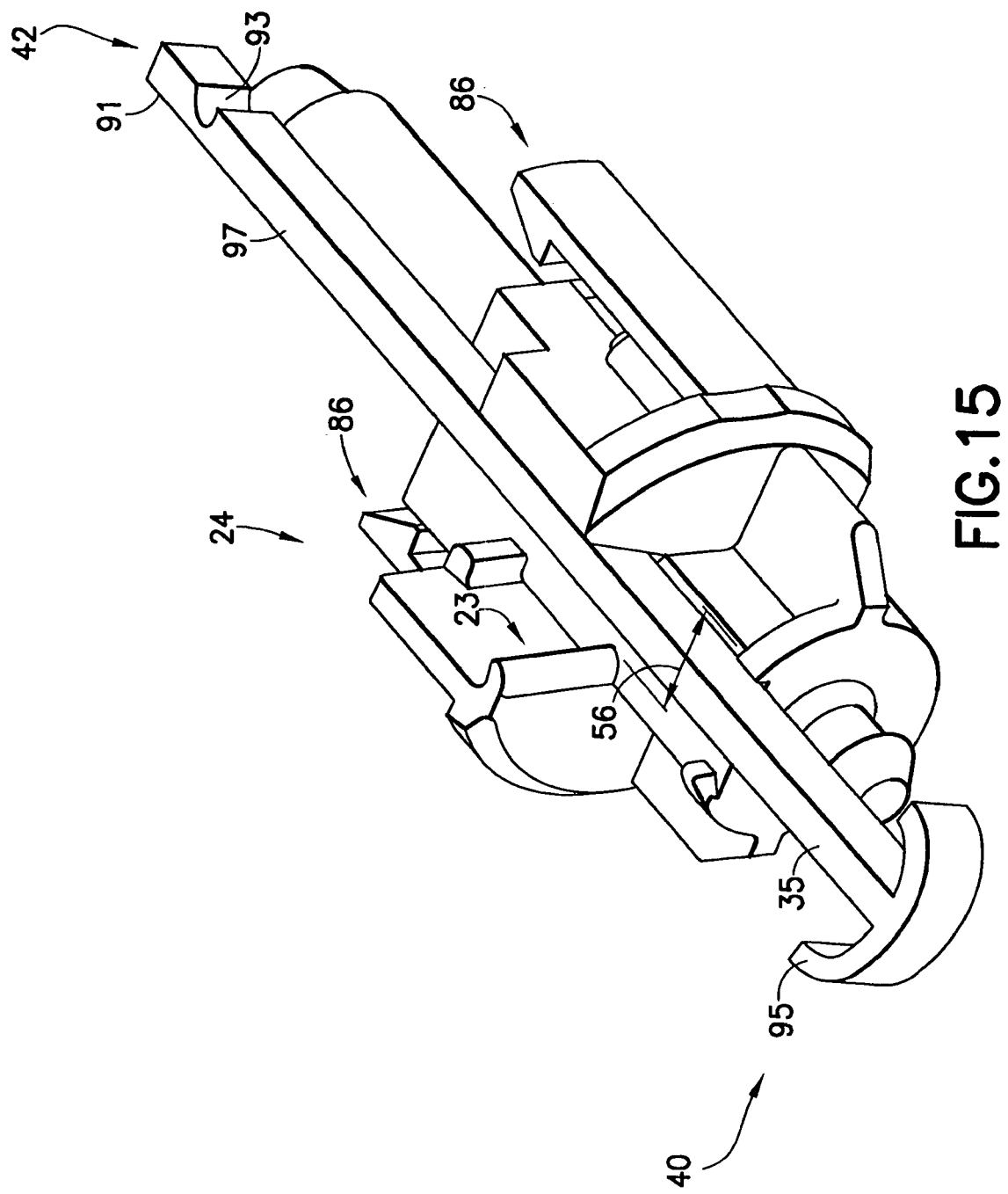
FIG. 15 is a perspective view of a hub and a portion of a retaining member of the present invention.
Figure 16:
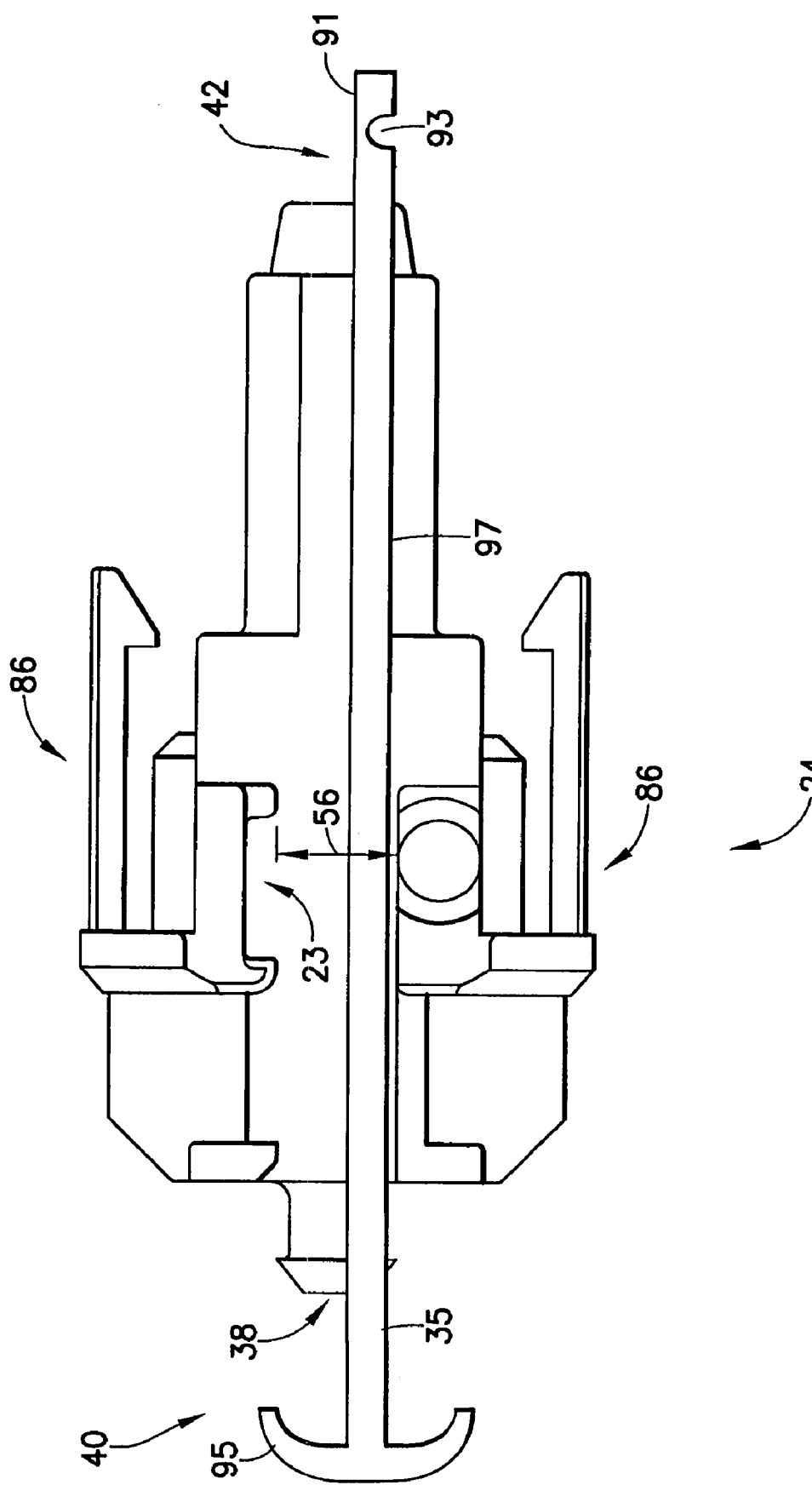
FIG. 16 is a side elevational view of the hub and retaining member of FIG. 15.

Needle hub 24 is illustrated in greater detail in FIGS. 15 and 16. Needle hub 24 includes a proximal end 40, a distal end 42, and a lumen 38 extending therebetween. Housing attachment means is provided externally of hub 24 to achieve fixed engagement between hub 24 and needle housing 80. The housing attachment means may include ultrasonic welding, heat staking, solvent bonding, mechanical latches with receiving latch detents, adhesive bonding, friction fitjoints, irreversible threads, or any of the like. In the embodiment of FIGS. 5, 6, 7, 15, and 16, the housing attachment means are defined by mechanical latches 86 that extend distally from needle hub 24 for engagement in detents 88 on needle housing 80. Hub 24 is mounted securely to locations on needle cannula 22 between proximal and distal ends 34 and 36 thereof, and in a specified rotational orientation relative to the bevel at distal end 36 of needle cannula 22. More particularly, an adhesive well is formed on needle hub 24 and receives adhesive to bond needle cannula 22 to hub 24. Alternately, needle hub 24 and needle housing 80 may be combined as one molded component. However, it is generally easier to manufacture needle hub 24 and housing 80 as two components. The housing 80 may be considered an extension of or part of the hub 24, particularly in connection with the retaining member 35.

Needle housing 80 is illustrated in greater detail in FIGS. 11A-11C. Needle housing 80 includes a proximal end 82, a distal end 84, and a tubular wall 44 extending between ends 82 and 84. As shown in FIGS. 11A-11C, tubular wall 44 is of generally circular or elliptical cross-section. Alternately, tubular wall 44 may have a non-circular cross-section or rectangular cross-section. The specific cross-sectional shape is not critical, and shapes other than those shown herein are contemplated. Housing 80 preferably is formed from a transparent or translucent material to permit user observation of safety shield 28. Thus, the medical practitioner can observe movement of safety shield 28, as explained below, to provide a visual indication that proper shielding is taking place. Additionally, proximal end 82 of housing 80 may have one of many optional means for attachment to a needle holder 12, such as a threaded connection, interference fit, adhesive bonding, solvent bonding, ultrasonic welding, heat staking, snap fit, or any other means. More specifically, the housing may have external threads and may be mounted to internal threads of the distal end of the needle holder. Alternately, housing 80 has non-threaded mounting means to engage holder 12 in an interlocking manner. External rings 81 are illustrated in FIGS. 5-7 and define one preferred non-threaded mounting means that provide sufficient friction or interlocking forces to resist housing 80 from unintentionally releasing from holder 12 during puncturing of septum 21 by proximal end 34 of needle cannula 22. In the illustrated embodiment, hub 24 is mounted indirectly to the holder 12 through needle housing 80. Housing 80 preferably is non-rotatably mounted to holder 12 to ensure that the bevel at distal end of needle cannula 22 faces up relative to the bottom edge of flange 17 of holder 12. Distal end 84 of needle housing 80 is characterized by diametrically opposed V-shaped notches 85 as shown in FIG. 11 B. Notches 85 cooperate with corresponding structure on packaging shield 26.

Housing 80 has a length such that distal end 84 of housing 80 is spaced proximally from distal end 36 of needle cannula 22 sufficiently to enable convenient use of needle cannula 22. Portions of tubular wall 44 from distal end 84 toward proximal end 82 of hub 24 are spaced outwardly from needle cannula 22 for permitting telescoped movement of safety shield 28 between needle cannula 22 and housing 80, as explained further below. Additionally, as shown in FIGS. 1, 3, and 4, tubular sidewall 44 of housing 80 is provided with external surface configurations or grips 46 include elongate recesses or flats having small bumps thereon. However, other surface configurations may be employed, such as a plurality of ridges or grooves, or concave detents shaped to conform to a user's fingers. Grips 46 preferably are orthogonal to the bottom edge of finger flange 17 of holder 12.

Housing 80 has internal features to restrict movement of safety shield 28 relative to housing 80. Tubular wall 44 of housing 80 is formed with a first proximal facing stop surface 48. As shown in FIG. 11B, housing 80 further includes an axially extending latch channel 52 formed on an interior surface of tubular wall 44. Latch channel 52 extends from the first proximal facing stop surface 48 shown in FIG. 11C to a location substantially adjacent distal end 84 of housing 80 as shown in FIG. 11B. A distal detent 47 is located near the distal end of tubular wall 44 of housing 80, as shown, and is at the distal end of latch channel 52. Distal detent 47 has a distally facing stop surface 54. Distal detent 47 and distally facing stop surface 54 are dimensioned to receive a latch 68 on safety shield 28, as explained below. Tubular wall 44 further includes a stop channel 50 extending distally and ending with a second proximally facing stop surface 58 near distal end 82 of housing 80 as shown in FIG. 11C.

Distal end 36 of needle cannula 22 is used to pierce the patient's skin and must be kept very sharp. Thus, a packaging shield 26, as shown in FIGS. 1-3 and 8-10, is used to enclose the distal end 36 of needle cannula 22. The packaging shield 26 preferably is formed with two opposing relatively flat walls 19 to facilitate easy handling by the phlebotomist who is likely to be wearing gloves that may even be wet with alcohol prep solution. In the embodiment shown, the open end of the packaging shield 26 fits partially over the distal end 84 of housing 80. The packaging shield 26 and housing 80 are dimensioned so that there is an interference fit that desirably provides a sterile barrier between the packaging shield 26 and housing 80 in those embodiments that do not employ blister packaging. In those embodiments, the interference fit between packaging shield 26 and housing 80 may make separation of packaging shield 26 difficult. Accordingly, for those embodiments, packaging shield 26 is provided with a pair of diametrically opposed ribs (not shown) on the interior surface. The ribs terminate at a V-shaped point or an arcuate end facing toward the open end of packaging shield 26. The ends of the ribs are disposed, dimensioned, and configured to mate with the V-shaped notches 85 at distal end 84 of housing 80. The engagement of the ends of the rib with V-shaped notches 85 develops ramping forces in response to twisting of packaging shield 26. Thus, the rotational movement applied to packaging shield 26 generates a corresponding axial movement of packaging shield 26 relative to housing 80, and hence facilitates separation of packing shield 26. Additionally, a tamper-evidence indicator may be placed between the packaging shield 26 and the housing 80 to provide indication of prior usage.

Safety shield 28, as shown in FIGS. 12A-12D, includes a proximal end 60, a distal end 62, and a substantially tubular sidewall 64 extending between the ends. Tubular sidewall 64 of safety shield 28 preferably is imprinted with indicia at a location aligned with the bevel-up side of needle cannula 22. This is the portion of tubular sidewall 64 that will be the most visible to the medical practitioner. The existence of indicia on this portion of tubular sidewall 64 provides a physical indication to the medical practitioner that shielding is taking place. The indicia should be in a form that will provide evidence of movement. For example, a plurality of intermittent markings or a marking that changes its dimensions along its length would be most beneficial. Safety shield 28 initially is retained releasably in a proximal position with at least a major portion of safety shield 28 disposed in the space between needle cannula 22 and tubular wall 44 of housing 80. In this proximal position, proximal end 60 of safety shield 28 is substantially adjacent first proximally facing stop surface 48 of housing 80. Additionally, as shown in FIG. 1, distal end 62 of safety shield 28 is flush with or projects only slightly from distal end 84 of housing 80 when safety shield 28 is in its proximal position. Safety shield 28 can be released from its proximal position and is movable to a distal position that is shown in FIGS. 4, 18, 19C, and 20C. When moved into its distal position, safety shield 28 completely covers portions of needle cannula 22 between needle hub 24 and distal end 36 of needle cannula 22.

Figure 12B:
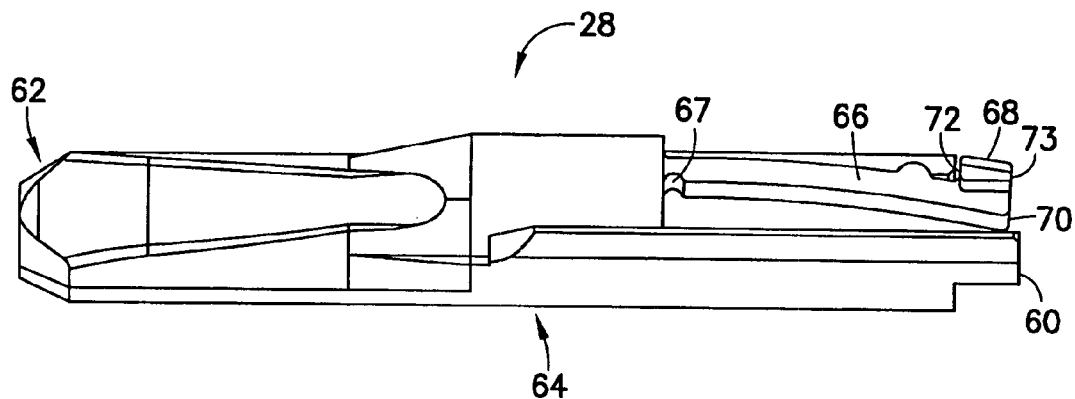
Figure 12C:
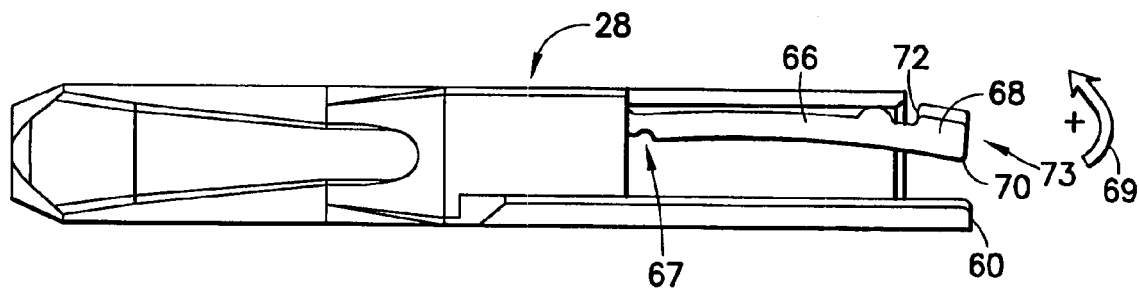
FIG. 12C is a side elevational view of the safety needle shield of FIGS. 12A and 12B with a deflectable member in an unbiased position.
Figure 12D:
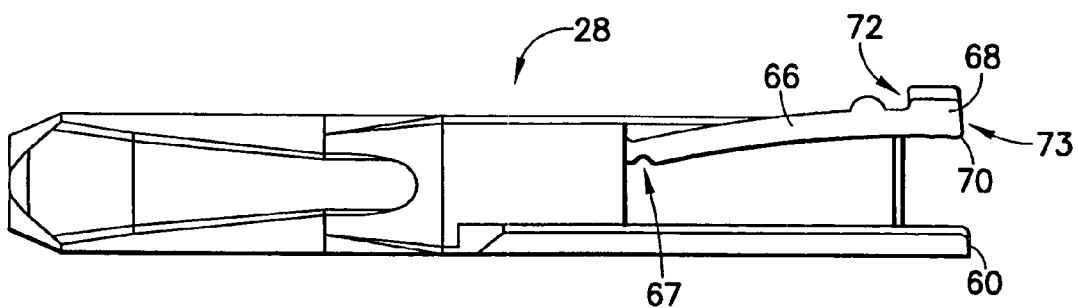
FIG. 12D is a side elevational view of the safety needle shield of FIGS. 12A and 12B with the deflectable member in a biased position.

As shown in FIGS. 12B-12D, safety shield 28 has a hinged deflectable member 66 that is cantilevered toward proximal end 60. Deflectable member 66 is deflectable outwardly or in a transverse direction. A locking lug or latch 68 is formed on deflectable member 66 near proximal end 60 of safety shield 28 and enters latch channel 52 when deflectable member 66 is deflected outwardly. Hinged deflectable member 66 further includes a cam surface 70 at the extreme proximal end thereof. Cam surface 70 is aligned at an acute angle to a radial plane passing through needle assembly 10. Axially aligned distally directed forces on cam surface 70 will generate a transverse deflection of deflectable member 66 so that latch 68 enters into latch channel 52. Latch 68 further includes a distal facing locking face 72, and a proximally facing locking face 73. Both locking faces 72 and 73 are aligned substantially perpendicular to the axis of needle assembly 10. FIG. 12C shows deflectable member 66 in its non-deflected state and FIG. 12D shows deflectable member 66 in its deflected state. Distal movement of actuator 30 moves deflectable member 66 from the position shown in FIG. 12C in direction 69 depicted in FIG. 12C to the position shown in FIG. 12D until latch 68 is no longer resisted by first proximally facing stop surface 48 of housing 80 and therefore is free to move distally with respect to the needle cannula 22 under spring energy supplied by spring 32.

Safety shield 28 further includes a stop 74 disposed substantially diametrically opposite latch 66. Stop 74 is in a plane passing through the axis of needle assembly 10 and includes a locking surface 76 facing in the distal direction as shown in FIG. 12A. Stop 74 prevents spring 32 from pushing safety shield 28 past housing 80.

Hub 24 is connected to the proximal end 82 of housing 80. Hub 24 further includes an actuator channel 56 extending substantially parallel to housing 80 as shown in FIGS. 15 and 16. Actuator 30, as shown in FIGS. 13 and 14, is disposed slidably in actuator channel 56 of hub 24. Actuator 30 includes a proximal end 78 substantially adjacent to needle cannula 22 that will lie within needle holder 12. Actuator 30 also includes a distal end 79 that will lie substantially adjacent cam surface 70 of latch 68. Distal end 80 of actuator 30 is angularly aligned to mate with cam surface 70 of latch 68, such that distal movement of actuator 30 will generate transverse deflection of deflectable member 66.

As shown in FIGS. 13 and 14, actuator 30 has an integrated anti-reset feature or latch 29 that interfaces with hub 24 upon activation of the device. Once a tube 20 is inserted and interfaces with the proximal end 78 of actuator 30, latch 29 will interface with the hub channel 56 thus deforming latch 29 temporarily inward thereby permitting latch 29 to advance into latch recess 23. Once latch 29 is within latch recess 23, latch 29 will return resiliently towards an undeflected position so that actuator 30 is prevented from moving back to a proximal position that would allow safety shield 28 to be completely reset to its original position.

A spring 32 surrounds portions of needle cannula 22 that are surrounded by safety shield 28. Thus, spring 32 is compressed to retain stored energy when safety shield 28 is in proximal position within tubular wall 44 of housing 80. Spring 32 then will propel safety shield 28 distally after activation. The proximal end 31 of spring 32 remains in fixed relation to the holder 12, hub 24, and housing 80 while the distal end 33 of spring 32 moves relative to the holder 12, hub 24, and housing 80.

The force applied by spring 32 to safety shield 28 is essential to proper operation of needle assembly 10. In particular, spring 32 must exert sufficient force to ensure that safety shield 28 will be propelled sufficiently toward distal end 32 of needle cannula 22 to complete its essential shielding function. A spring force of 0.02-0.20 pounds, and preferably about 0.09 pounds, has been found to meet the objectives of ensuring complete shielding without excessive force. Additionally, a fine lubricating spray may be applied to the sliding parts of safety shield 22, hub 24, and/or housing 80 to ensure complete and efficient movement of safety shield 28 and a low spring force.

Needle assembly 10 is used by attaching proximal end of hub 24 and housing 80 into needle holder 12 such that proximal end 23 of needle cannula 22 and proximal end 78 of actuator 30 lie within needle holder 12. Packaging shield 26 then is removed from housing 80 to expose pointed distal end 36 of needle cannula 22. The medical practitioner then manually engages housing 80 at grips 46 and guides distal end 32 of needle cannula 22 into a targeted vein of a patient. Activation of shield 28 is achieved automatically and passively by insertion of blood collection tube 20 into proximal end 14 of needle holder 12. Sufficient insertion of blood collection tube 12 will cause proximal end 14 of needle cannula 22 to pierce through the elastomeric septum 21 that extends across the open end of blood collection tube 20, as shown in FIGS. 19A-19C. Distal movement of blood collection tube 20 into needle holder 12 also will cause blood collection tube 20 to engage proximal end 78 of actuator 30, thereby causing actuator 30 to slide distally through actuator channel 56 of hub 24. This distal movement of actuator 30 will cause distal end 79 of actuator 30 to engage cam surface 70 of hinged deflectable member 66 of safety shield 28 with sufficient force to pivot deflectable member 66 transversely about hinge 67 sufficiently to disengage locking face 72 of latch 68 from first proximally facing stop surface 48 of housing 80.

A further feature of the present invention is the provision of a retaining member 35, in which the present invention provides for engaging the telescoping shield 28 with the retaining member 35 upon insertion of the evacuated tube 20 in the needle holder 12, wherein the retaining member 35 prevents the telescoping shield 28 from moving to a needle cannula encapsulating position with the retaining member 28 engaged.

In particular, as seen in FIGS. 19A-19C, the retaining member 35 includes at least one retaining arm 97 slidably mounted with respect to the hub 24. The retaining member 35 extends longitudinally within holder 12 with a first end supported adjacent proximal end 78 of actuator 30, and an opposed end extending adjacent at least one locking lug or latch 68 of the actuating arm, i.e., deflectable member 66. The retaining arm 97 of the retaining member 35 engages locking lug or latch 68 after the actuating arm (i.e., deflectable member 66) has disengaged the latch 68 from its original position as shown in FIG. 19B. The retaining member 35 is omitted from the actuation sequence shown in FIGS. 20A-20C for clarity of the actuator operation. Although FIGS. 19A-19C and FIGS. 26A and 26B depict one embodiment of retaining arm 97 for illustrative purposes, other configurations are considered within the scope of the present invention. Retaining arm 97 of retaining member 35 includes a mating surface 91 for engagement between the retaining arm 97 and the latch 68. Mating surface 91 may include a cam surface, which may assist in the disengagement of the retaining arm 97 from the latch 68 upon withdrawal of the tube 20 from the needle holder 12. Retaining arm 97 desirably includes a living hinge 93 incorporated into the retaining arm 97, which cooperates with the structure of the channel formed in the housing 80, such as shoulder 83 within housing 80. As used herein, the hub 24 may include a number of separate components such as the housing 80.

An important feature of the present invention is that when the retaining arm 97 is engaged with the latch 68, the telescoping shield 28 is activated (i.e., out of the locked position) and the engagement is sufficient to prevent the spring 32 from advancing the telescoping shield 28. In other words, the activated telescoping shield 28 will not be deployed until the retaining arm 97 is disengaged from the latch 68 (also referred to as locking lugs).

The retaining member 35 further includes a biasing member 95, biasing the retaining arm 97 away from engagement with the latch 68. The biasing force of biasing member 95 can be exerted from the resiliency of the material forming the retaining member 35, or may be present through a separate member such as a leaf spring or a coil spring, or the like. The biasing member 95 is positioned such that the biasing member 95 is biased against its natural bias between a blood collection tube 20 and shoulder 13 extending radially within holder 12 when a blood collection tube 20 is inserted within holder 12 for sampling purposes. As such, the biasing member 95 is prevented from moving the retaining arm 97 away from engagement with the latch 68 while the tube 20 is in the needle holder 12. With the withdrawal of the tube 20 from the needle holder 12, the biasing member 95 will disengage the retaining arm 97 from the latch 68, and the spring 32 will then fully deploy the telescoping shield 28.

The activation of the telescoping shield 28 of the needle assembly 10 is triggered by the insertion of an evacuated blood collection tube 20 having a closure such as septum 21 into needle holder 12, when a top surface of septum 21 compresses multiple sample sleeve 39 after it has been penetrated by proximal end 34 of needle cannula 22. This action will also serve to actuate the actuator 30 as discussed above, and to engage the retaining member 35 with the telescoping shield 28.

Retaining member 35 is designed so as to maintain the telescoping shield 28 in the retracted position even after the telescoping shield 28 has been activated through actuator 30, so long as a tube is exerting a force against the natural bias of biasing member 95. Since activation of actuator 30 occurs through insertion of a tube 20 into needle holder 12, such tube 20 also engages the retaining member 35, causing biasing member 95 to be pressed against shoulder 13, and to be stressed against its natural bias. As such, the telescoping shield 28 is free from engagement of the locking assembly holding it in place in the retracted position, but is still retained in the retracted position due to the interaction of mating surface 91 of retaining member 35 and latch 68. More particularly, once actuator 30 activates the telescoping shield 28, the retaining member 35 is advanced such that mating surface 91 is longitudinally forced against shoulder 83 of housing 80. This movement causes the retaining arm 97 to bend through living hinge 93, such that mating surface 91 is moved into engagement with latch 68.

Once the tube 20 is removed from the needle holder 12, the stress force exerted against biasing member 95 of retaining member 35 is released, thereby allowing biasing member 95 to return to its natural bias, as shown in FIG. 19C. This action causes retaining member 95 to be moved out of engagement with the latch 68, thereby permitting telescoping shield 28 to be propelled to the fully extended position due to the bias of spring 32.

The biasing force of spring 32 causes telescoping shield 28 to be propelled to the fully extended position should be less than the force needed to disengage retaining member 35 out of engagement with latch 28. This ensures that the retaining member 35 will be able to retain the telescoping shield in the retracted position until it is disengaged upon removal of tube 20. The biasing force of biasing member 95 should be sufficiently strong so as to ensure that retaining member 35 is moved out of engagement with latch 68 upon removal of tube 20. The specific design of retaining arm 97 of retaining member 35 can function to this effect. For example, retaining arm 97 may have inherent flexibility therein so that it can flex outwardly out of engagement from latch 68. Alternatively, mating surface 91 may be a cammed surface, which further facilitates the ability for retaining arm 97 to move out of engagement, such as through a rotation of retaining member 35 upon removal of tube 20. Alternatively, the living hinge 93 may act as a flexing portion of retaining arm 97 to permit it to move out of engagement with latch 68 upon force extended through biasing member 95 upon removal of tube 20.

The present invention, therefore, permits the user to perform the medical procedure without changing their normal sequence of operation, since no conscience action is needed to activate or otherwise control telescoping shield 28. It should be understood that telescoping shield 28 is triggered merely by pushing the closure of a tube 20 onto the proximal end 36 of the cannula 22 and/or compressing the multiple needle sleeve 39. After the actuator 30 has triggered the transported telescoping shield 28, the retaining member 35 prevents deployment until the retaining member 35 is disengaged from the latch 68, which occurs automatically upon tube 20 withdrawal from the needle holder 12. With the disengagement of the retaining member 35 from the latch 68, the telescoping shield 28 is moved from the retracted position shown in to a partially extended position against the patient (if the needle is still inserted at time of tube withdrawal), and then to the fully encapsulated position upon needle withdrawal.

Disengagement of latch 68 from first proximally facing stop surface 48 into latch channel 52 and disengagement of the retaining member 35, causes safety shield 28 to be propelled distally under the action of spring 32. Latch 68 will be guided in latch channel 52 as safety shield 28 is moved toward distal end 84 of housing 80. Sufficient distal movement of safety shield 28 will cause latch 68 to engage in distal detent 47 of housing 80. While in distal detent 47, latch 68 interferes with distal facing stop surface 54 and prevents safety shield 28 from being unshielded. Additionally, stop 74 on safety shield 28 rides along stop channel 50 until stop 74 engages second proximally facing stop surface 58 thereby preventing safety shield 28 movement in the distal direction after needle point 36 has been shielded. As a result of stop 74 and latch 68, safety shield 28 is prevented from moving either distally or proximally from this locked position as shown in FIGS. 18, 19C, and 20C.

The above-described needle assembly is completely passive in that shielding is achieved without any required user activation other than the normal insertion and withdrawal of a fluid collection tube 20 into the open proximal end 14 of holder 12.

There may be instances, however, where a user may want direct control over the initiation of shielding, or where a user may want dual control where shielding can be actuated by insertion of a fluid collection tube and/or by direct digital activation by the user. These options can be achieved without a complete redesign of the above-described needle assembly. In particular, an alternate needle assembly is identified generally by the numeral 10a in FIGS. 12-25. Assembly 10a includes a needle cannula 22, a hub 24, a packing shield 26, and a housing 80, all of which are substantially identical to corresponding parts of the first embodiment described and illustrated above. However, assembly 10a includes a holder 12a that is slightly different from holder 12 described and illustrated above. Holder 12a includes a tubular sidewall 18a that has a proximal end 14a, a distal end 16a, and a tubular sidewall 18a. A notch 17a extends into tubular sidewall 18a at distal end 16a. Additionally, notch 17a is disposed on a portion of sidewall 18a that will align with the bevel-up side of needle cannula 22. Notch 17a is partly surrounded by an elongate flat or recess 19a in tubular sidewall 18a to minimize the projection of an actuator, as explained herein and to provide a visible indication of a region to be accessed by a user for carrying out a manual actuation of the shielding.

Needle assembly 10a further includes an actuator 30a that differs from actuator 30 described and illustrated above. In particular, actuator 30a includes an actuating beam 31a with a distal end 79a that is structurally and functionally virtually identical to distal end 79 of actuator 30 described and illustrated in FIGS. 13 and 14. Additionally, actuating beam 31a includes an anti-reset latch 29a that is functionally substantially identical to latch 29 of actuator 30. Actuator 30a further includes a mounting collar 77a that is disposed and configured to mount slidably over proximal portions of hub 24 and further includes a proximal end 78b that is identical to proximal end 78 of actuator 30. Additionally, mounting collar 77a is dimensioned for slidable disposition within holder 12a. Actuator 30a further includes an arm 90a that projects distally from collar 77a. Arm 90a is dimensioned for slidable insertion in notch 17a of holder 12a, and terminates at an actuating button 92a.

Needle assembly 10a is assembled substantially as needle assembly 10 described and illustrated above. However, collar 77a of actuator 30a is slidably disposed over and around proximal portions of hub 24a. The subassembly of needle cannula 22, hub 24, packing shield 26, holder 80, and actuator 30a can be mounted in holder 12a substantially as described above. However, arm 90a will project slidably through notch 17a such that actuating button 92a is slidably disposed on the outer circumferential surface of holder 80a.

Needle assembly 10a is used substantially in the conventional manner as explained above. However, safety shield 28 may also be actuated by digital pressure exerted by a thumb or forefinger of the user on actuator button 92a. In particular, if the user urges actuator button 92a distally along outer surface of holder 80, a sufficient distance for distal end 79a of actuator 30a to actuate safety shield 28, the safety shield will be actuated. Actuator 30a permits shielding to be completed either by insertion of an evacuated tube into holder 80 or by digital pressure on actuator button 92b. The retaining member 35 further includes a biasing member 95, which performs the same function as described in the previous embodiments.

The internal disposition of safety shield 28 within the housing in any of these embodiments provides several significant advantages. In particular, a medical practitioner employing needle assembly 10 can hold needle assembly 10 much closer to distal end 32 of needle cannula 22. This distal location for gripping needle assembly 10 provides better balance and feel for the medical practitioner and facilitates alignment and aiming of needle assembly 10.

Alternately to the embodiments described above, the needle assembly can be made in a detachable holder or hard pack assembly 100 configuration using all the components of the needle assembly described above with the addition of a non-patient needle shield 90 for enclosing proximal end 34 of needle cannula 22 shown in FIGS. 8-10. Non-patient needle shield 90 is reversibly detachable to one or both of needle housing 80 and hub 24. The user removes non-patient needle shield 90 from hardpack assembly 100 and attaches holder 12 to the proximal end of housing 80 prior to use. Once holder 12 is attached to housing 80, the user can remove packaging shield 26 and use the needle device in a similar manner to the needle assembly embodiment described herein.

Figure 27:
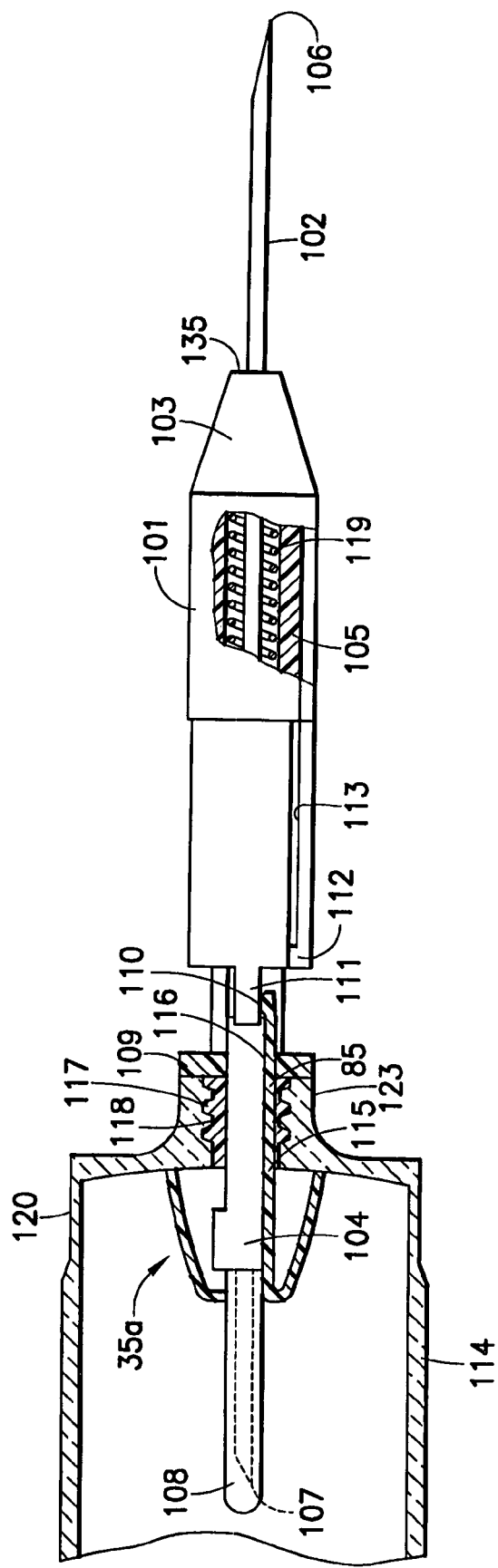
FIG. 27 is a perspective schematic view of another embodiment of the present invention.

FIG. 27 is a perspective view of a passively shielded needle assembly 100 according to another embodiment of the present invention in a starting retracted position. Assembly 100 includes a needle cannula 102 mounted in a hub 105 having a telescoping shield 103 mounted thereon for movement from a starting retracted position to an activated nondeployed position through a venipuncture partially extended position to a fully extended and locked position covering a distal end 106 of needle cannula 102. A proximal end 107 of needle cannula 102 is encompassed by an elastomeric or rubber multiple sample sleeve 108 that is attached to a distal end of hub 105 to seal proximal end 107 and prevent fluid from flowing through cannula 102. The details of the structure of the hub 105, an actuator 104, and the telescoping shield 103 are described in detail in U.S. Pat. Nos. 5,718,239 and 5,893,845 and are incorporated herein by reference. A further key feature of the present invention is the provision of a retaining member 35a, in which the present invention provides for engaging the telescoping shield 103 with the retaining member 35a upon insertion of the evacuated tube in the needle holder 120, wherein the retaining member 35a prevents the telescoping shield 103 from moving to a needle cannula encapsulating position with the retaining member 35a engaged. The retaining member 35a is essentially the same as retaining member 35 discussed above.

The retaining member 35a includes at least one retaining arm 97a slidably mounted on the hub 105. The retaining arm 97a of the retaining member 35a engages at least one locking lug 111 after the actuating arm 115 has disengaged the locking lug 111 from the locking recess. The important feature of the present invention is that when the retaining arm 97a is engaged with the locking lugs 111, the telescoping shield 108 is activated (i.e. out of the locked position) and the engagement is sufficient to prevent the spring 119 from advancing the telescoping shield 103. In other words, the activated telescoping shield 103 will not be deployed until the retaining arm 97a is disengaged from the locking lugs 111. The retaining member 35a further includes a biasing member 95a biasing the retaining arm 97a away from engagement with the locking lug 111. The biasing member 95a can be formed from the resiliency material forming the retaining member 35a, or may be a separate member such as a leaf spring or a coil spring, or the like. The biasing member 95a is positioned such that the biasing member 95a is prevented from moving the retaining arm 97a away from engagement with the locking lug 111 while the tube is in the needle holder 120. With the withdrawal of the tube from the needle holder 120, the biasing member will disengage the retaining arm 97a from the locking lug 111 and the spring will then deploy the telescoping shield 103.

The above described needle assembly 100, with its telescoping shield 103, may be used by a phlebotomist in the following manner and method. After a user has removed needle assembly 100 from its sterile package, it is snap mounted or screw mounted onto distal end of needle holder 120. The user then prepares a venipuncture site on the patient's skin and applies a tourniquet prior to venipuncture. Venipuncture is then performed by inserting distal end 106 of needle cannula 102 into patient's skin and into a vein. When distal end 106 has been properly inserted and evacuated blood collection tube with its closure is inserted into open end 122 of needle holder 120, closure is then punctured by proximal end 107 of needle cannula 102. When puncture of the closure has occurred sufficiently to contact and move actuator 104 in a distal direction, cam face 110 on arm 115 of actuator 104 meets with mating surface 116 on lug 111 of shield 103 to cause shield 103 to rotate and to activate transportation of shield 103. Simultaneous with the movement of the actuator 104, the retaining member 35a will be advanced by the closure to engage retaining arm 97a with the lug 111 preventing movement of the telescoping shield 103 in the distal direction toward the venipuncture site. Upon removal of the tube, the biasing member 95a will disengage the retaining member 35a from the telescoping shield 103 allowing further deployment of the shield 103.

In addition to activating telescoping shield 103, when proximal end 107 enters into evacuated tube body fluid, flows through cannula 102 into the evacuated tube and when sufficient body fluid has been received, the user can remove evacuated tube from tube holder 120 which will deploy the telescoping shield 103 as described above. The user can continue drawing body fluid with additional evacuated blood collection tubes with the telescoping shield in a partially extended position adjacent the patient's skin. When the evacuated blood collection tube is removed from needle holder 120, multiple sample sleeve 108 returns to its original position to close and seal distal end 107 of cannula 102 and stops the flow of body fluid through cannula 102. When no more body fluid is desired to be collected, needle cannula 102 is withdrawn from the patient's vein and skin permitting shield 103 to further extend to the fully extended, and preferably locked position where distal end of shield 103 extends beyond and sufficiently shields distal end 106 of needle cannula 102.

In the foregoing discussion, it is to be understood that the above-described embodiments of the present invention are merely exemplary. For example, the distal locking pocket can alternatively be located linearly in the channel at the distal end of the needle hub to alleviate the need for rotation by the torsion spring. In addition, of course, the present invention is not limited to activation by a blood collection tube. Other suitable variations, modifications, and combinations of the above described features could be made to, or used in these embodiments and still remain within the scope of the present invention. It is intended that the invention be construed as including all such modifications and alterations. The scope of the present invention is intended to be defined by the appended claims and all equivalents thereof.

What is claimed is:

1. A shieldable needle assembly comprising:

a needle cannula having a proximal end and a distal end;

a hub mounted to the needle cannula at a location spaced from the distal end;

a shield axially slidable over the needle cannula between a fully retracted position and a fully extended position encapsulating the distal end of the needle cannula;

a first biasing member biasing the shield towards the fully extended position;

a lock, comprising a releasable abutting engagement with the shield, for releasably maintaining the shield in the fully retracted position;

an actuator for releasing the lock; and a retaining member, comprising a releasable abutting engagement with the shield, distinct from the abutting engagement of the lock,
wherein after activation of the actuator and release of the abutting engagement of the lock, retaining member engages the shield, and wherein the shield is prevented from moving to the fully extended position until the abutting engagement of the retaining member is disengaged from the shield.

2. The apparatus of claim 1, wherein the actuator includes at least one actuating arm slidably mounted on the hub for releasing the lock 3. The apparatus of claim 2, wherein one of the hub and the shield includes a latch, and wherein the other of the hub and the shield includes a detent for releasably engaging the latch, the latch and the detent forming the lock for releasably maintaining the shield in the fully retracted position, and wherein the actuating arm disengages the latch from the corresponding detent to release the lock.

4. The apparatus of claim 3, further comprising a housing projecting from the hub toward the distal end of the needle cannula and spaced outwardly from the needle cannula.

5. The apparatus of claim 3, wherein the shield includes a latch and wherein the hub includes a detent for releasably engaging the latch.

6. The apparatus of claim 3, wherein the retaining member includes a retaining arm slidably mounted on the hub, wherein the retaining member engages a retaining lug on the shield after the actuating arm has disengaged the latch from the detent.

7. The apparatus of claim 6, further including a second biasing member biasing the retaining arm away from engagement with the retaining lug.

8. The apparatus of claim 7, wherein the second biasing member is positioned such that the second biasing member is prevented from moving the retaining arm away from engagement with the retaining lug for a period of time following activation of the actuator.

9. The apparatus of claim 8, wherein said hub is adapted to mate with a needle holder, and wherein the actuator is activated by pressure applied through insertion of a sampling container within the needle holder.

10. The apparatus of claim 9, wherein the second biasing member biases the retaining arm away from engagement with the retaining lug upon withdrawal of the sampling container from the needle holder.

11. The apparatus of claim 10, wherein the first biasing member is a spring, wherein the spring has a spring force less than the force required to disengage the retaining arm away from engagement with the retaining lug.

12. The apparatus of claim 10, further including a second lock securing the shield in the fully extended position.

13. The apparatus of claim 1, wherein the retaining member includes a retaining arm slidably mounted on the hub, and wherein the retaining member engages the shield after the actuator has disengaged the lock.

14. The apparatus of claim 13, further including a second biasing member biasing the retaining arm away from engagement with the shield.

15. The apparatus of claim 14, wherein the second biasing member is positioned such that the second biasing member is prevented from moving the retaining arm away from engagement with the shield for a period of time following activation of the actuator.

16. The apparatus of claim 15, wherein the hub is adapted to mate with a needle holder, and wherein the actuator is activated by pressure applied through insertion of a sampling container within the needle holder.

17. The apparatus of claim 16, wherein the second biasing member biases the retaining arm away from engagement with the shield upon withdrawal of the sampling container from the needle holder.

18. The apparatus of claim 17, wherein the first biasing member is a spring, and wherein the spring has a spring force less than the force needed to disengage the retaining arm away from engagement with the shield.

19. A blood collection assembly comprising: a needle cannula;
a hub mounted on the needle cannula;
a spring biased telescoping shield mounted on the hub and slidable between a fully retracted position and a frilly extended position encapsulating a distal end of the needle cannula;
a needle holder having a first end mated with the hub and a second end adapted for receiving a blood collection container; and
a retaining member moveably mounted on the hub and engageable with the telescoping shield when a blood collection container is received in the needle holder,
wherein the retaining member holds the telescoping shield from moving toward the fully extended position when engaged therewith, and wherein removal of the blood collection container from the needle holder causes the retaining member to disengage from the telescoping shield, thereby releasing the telescoping shield such that the telescoping shield will move toward the fully extended position.

20. The apparatus of claim 19, wherein the retaining member includes a retaining arm slidably mounted on the hub.

21. The apparatus of claim 19, further including a biasing member biasing the retaining arm away from engagement with the telescoping shield, wherein the biasing member is prevented from moving the retaining arm away from engagement with the telescoping shield until the blood collection container is removed from the needle holder.

22. A blood collection assembly comprising:
a needle cannula;
a hub mounted on the needle cannula;
a telescoping shield mounted on the hub and slidable between a fully retracted position and a fully extended position encapsulating a distal end of the needle cannula;
a spring mounted on the hub biasing the telescoping shield towards the fully extended position; a lock on the hub holding the telescoping shield in the fully retracted position;
a needle holder having a first end mated with the hub and a second end adapted for receiving a blood collection tube;
an actuator moveably mounted on the hub for releasing the lock, wherein the actuator is activated by insertion of a blood collection tube in the needle holder; and
a retaining member moveably mounted on the hub and engageable with the telescoping shield when a blood collection tube is positioned within the needle holder,
wherein insertion of a blood collection tube in the needle holder activates the actuator to cause the lock to be released from the retaining member holding the shield against the spring bias, and wherein removal of the blood collection tube from the needle holder disengages the retaining member from the telescoping shield, releasing the spring bias and allowing the telescoping shield to be moved in a direction toward the fully extended position.

23. The apparatus of claim 22, wherein the retaining member includes a retaining arm slidably mounted on the hub, and wherein the retaining arm engages the telescoping shield after the actuator has disengaged the lock.

24. The apparatus of claim 23, further including a biasing member biasing the retaining arm away from engagement with the telescoping shield, wherein the biasing member is prevented from moving the retaining arm away from engagement with the telescoping shield until the blood collection tube is removed from the needle holder.

25. The apparatus of claim 22, wherein the actuator includes an actuating arm slidably mounted on the hub for releasing the lock.

26. The apparatus of claim 25, wherein one of the hub and the telescoping shield includes a latch, and wherein the other of the hub and the telescoping shield includes a detent for releasably engaging the latch, the latch and the detent forming the lock for releasably maintaining the telescoping shield in the fully retracted position, and wherein the actuating arm disengages the latch from the corresponding detent to release the lock.

27. A method of safety shielding a needle comprising:
providing a needle assembly comprising a hub mounted to a needle cannula with a spring biased telescoping shield mounted on the hub and a retaining member moveably mounted on the hub;
providing a needle holder having a first end for mating with a needle assembly and a second end adapted for receiving a blood collection tube;
mating the needle assembly with the needle holder;
inserting a blood collection tube into the needle holder, thereby engaging the retaining member with the telescoping shield and causing the retaining member to prevent the telescoping shield from being biased to a shielded position encompassing the needle cannula; and
removing the blood collection tube from the needle holder, thereby disengaging the retaining member from the telescoping shield and causing the telescoping shield to be biased toward the shielded position encompassing the needle cannula.

28. The method of claim 27, further comprising the steps of releasably locking the telescoping shield in a fully retracted position with a first lock prior to engagement of the retaining member with the telescoping shield, and releasing the first lock upon insertion of the blood collection tube.

29. The method of claim 28, wherein the releasing of the first lock utilizes at least one actuating arm slidably mounted on the hub for releasing the lock.

30. The method of claim 29, wherein the actuating arm extends within the needle holder for engagement with the blood collection tube.

31. The method of claim 30, wherein one of the hub and the telescoping shield includes a latch, and wherein the other of the hub and the telescoping shield includes a detent for releasably engaging the latch, the latch and the detent forming the first lock for releasably maintaining the telescoping shield in the fully retracted position, and wherein the actuating arm disengages the latch from the corresponding detent to release the lock.

32. The method of claim 27, further including the step of biasing the retaining member away from engagement with the telescoping shield.

33. The method of claim 32, further including the step of preventing the biasing of the retaining member from moving the retaining member arm away from engagement with the telescoping shield while the blood collection tube is in the needle holder.

34. The method of claim 27, further including the step of locking the telescoping shield in the shielded position encompassing the needle cannula.

* * * * *